United States Patent
Chan et al.

(10) Patent No.: US 11,352,338 B2
(45) Date of Patent: *Jun. 7, 2022

(54) SUBSTITUTED ISOINDOLINONES

(71) Applicant: BioTheryX, Inc., San Diego, CA (US)

(72) Inventors: Kyle W. H. Chan, San Diego, CA (US); Aparajita Hoskote Chourasia, San Diego, CA (US); Paul E. Erdman, San Diego, CA (US); Leah M. Fung, San Diego, CA (US); Imelda Lam, San Diego, CA (US); Frank Mercurio, Rancho Santa Fe, CA (US); Robert W. Sullivan, Vista, CA (US); Eduardo Torres, San Diego, CA (US)

(73) Assignee: BioTheryX, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/912,330

(22) Filed: Jun. 25, 2020

(65) Prior Publication Data

US 2020/0325114 A1    Oct. 15, 2020

Related U.S. Application Data

(63) Continuation of application No. 16/681,180, filed on Nov. 12, 2019, now Pat. No. 10,844,039.

(60) Provisional application No. 62/760,813, filed on Nov. 13, 2018.

(51) Int. Cl.
  *C07D 401/04* (2006.01)
  *A61K 31/454* (2006.01)
  *C07D 403/04* (2006.01)

(52) U.S. Cl.
  CPC ......... *C07D 401/04* (2013.01); *C07D 403/04* (2013.01)

(58) Field of Classification Search
  CPC ..... C07D 401/04; A61K 31/454; A61P 35/00; A61P 25/28; A61P 29/00
  USPC .......................................... 546/201; 514/323
  See application file for complete search history.

(56) References Cited

U.S. PATENT DOCUMENTS

| | | | |
|---|---|---|---|
| 5,874,448 A | 2/1999 | Muller et al. | |
| 5,955,476 A | 9/1999 | Muller et al. | |
| 6,093,737 A | 7/2000 | Anthony et al. | |
| 6,458,810 B1 | 10/2002 | Muller et al. | |
| 7,323,479 B2 | 1/2008 | Zeldis | |
| 7,629,360 B2 | 12/2009 | Muller et al. | |
| 10,844,039 B2 * | 11/2020 | Chan ...................... | A61P 25/28 |
| 2001/0056109 A1 | 12/2001 | Huhtala et al. | |
| 2001/0056114 A1 | 12/2001 | D'Amato | |
| 2002/0173658 A1 | 11/2002 | Muller et al. | |
| 2003/0096841 A1 | 5/2003 | Robarge et al. | |
| 2003/0139451 A1 | 7/2003 | Shah et al. | |
| 2005/0004087 A1 | 1/2005 | D'Amato et al. | |
| 2005/0136065 A1 | 6/2005 | Valiante | |
| 2006/0052609 A1 | 3/2006 | Muller et al. | |
| 2006/0160854 A1 | 7/2006 | Muller et al. | |
| 2006/0199843 A1 | 9/2006 | Zeldis | |
| 2006/0211728 A1 | 9/2006 | Greig et al. | |
| 2006/0270707 A1 | 11/2006 | Zeldis et al. | |
| 2007/0190042 A1 | 8/2007 | Edinger et al. | |
| 2007/0244078 A1 | 10/2007 | Zeldis et al. | |
| 2008/0051432 A1 | 2/2008 | Zhang | |
| 2008/0064876 A1 | 3/2008 | Muller et al. | |
| 2009/0087407 A1 | 4/2009 | Zeldis et al. | |
| 2009/0155207 A1 | 6/2009 | Hariri et al. | |
| 2009/0171093 A1 | 7/2009 | Takeuchi et al. | |
| 2009/0232796 A1 | 9/2009 | Corral et al. | |
| 2010/0098657 A1 | 4/2010 | Schafer et al. | |
| 2011/0319271 A1 | 12/2011 | Park et al. | |
| 2012/0035068 A1 | 2/2012 | Ferguson et al. | |
| 2012/0192297 A1 | 7/2012 | Handa et al. | |
| 2012/0252844 A1 | 10/2012 | DeWitt | |
| 2013/0030021 A1 | 1/2013 | Muller et al. | |
| 2013/0143922 A1 | 6/2013 | Greig et al. | |
| 2016/0136146 A1 | 5/2016 | Chaudhary et al. | |
| 2018/0015087 A1 | 1/2018 | Liu et al. | |

(Continued)

FOREIGN PATENT DOCUMENTS

| | | |
|---|---|---|
| CN | 1405166 A | 3/2003 |
| CN | 1597680 A | 3/2005 |

(Continued)

OTHER PUBLICATIONS

Amit et al., "Axin-mediated CKI phosphorylation of β-catenin at Ser 45: a molecular switch for the Wnt pathway," Genes Dev. 2002, 16, 1066-76.
Bacauanu et al., "Metallaphotoredox difluoromethylation of aryl bromides," Angew. Chem. Inf. Ed. Engl. 2018, 57, 12543-8.
Baehr, "Membrane protein transport in photoreceptors: the function of PDEδ," Invest. Ophthalmol. Vis. Sci. 2014, 55, 8653-66.
Cheong and Virshup, "Casein kinase 1: complexity in the family," J. Biochem. Cell Biol. 2011, 43, 465-9.

(Continued)

*Primary Examiner* — Charanjit Aulakh
(74) *Attorney, Agent, or Firm* — Lin Yu, Esq.; Juniv LLP

(57) ABSTRACT

Substituted isoindolinones of Formula (I), methods of making such compounds, pharmaceutical compositions and medicaments comprising such compounds, and methods of using such compounds to treat or ameliorate diseases, disorders, or conditions associated with protein malfunction, such as cancer, are provided.

(I)

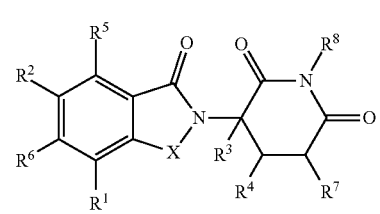

22 Claims, No Drawings

(56) References Cited

U.S. PATENT DOCUMENTS

| | | | |
|---|---|---|---|
| 2018/0085465 | A1 | 3/2018 | Bradner et al. |
| 2018/0228907 | A1 | 8/2018 | Crew et al. |

FOREIGN PATENT DOCUMENTS

| | | | | |
|---|---|---|---|---|
| CN | 107056772 | A | 8/2017 | |
| CN | 107698575 | A | 2/2018 | |
| CN | 107739389 | A | 2/2018 | |
| EP | 0383637 | A2 | 8/1990 | |
| EP | 1336602 | A1 | 8/2003 | |
| JP | 2000159761 | A | 6/2000 | |
| JP | 2005336157 | A | 12/2005 | |
| JP | 2009001528 | A | 1/2009 | |
| JP | 2009215195 | A | 9/2009 | |
| JP | 2011012014 | A | 1/2011 | |
| TW | I298724 | B | 7/2008 | |
| WO | 1998019649 | A2 | 5/1998 | |
| WO | 1999046258 | A1 | 9/1999 | |
| WO | 1999047512 | A1 | 9/1999 | |
| WO | 2002070480 | A1 | 9/2002 | |
| WO | 2005005409 | A1 | 1/2005 | |
| WO | 2006053160 | A2 | 5/2006 | |
| WO | 2006089150 | A2 | 8/2006 | |
| WO | 2007027527 | A2 | 3/2007 | |
| WO | 2008027542 | A2 | 3/2008 | |
| WO | 2012027065 | A2 | 3/2012 | |
| WO | 2014180882 | A2 | 11/2014 | |
| WO | 2015107196 | A1 | 7/2015 | |
| WO | 2016105518 | A1 | 6/2016 | |
| WO | 2016191178 | A1 | 12/2016 | |
| WO | 2017007612 | A1 | 1/2017 | |
| WO | 2017024317 | A2 | 2/2017 | |
| WO | 2017024318 | A1 | 2/2017 | |
| WO | 2017024319 | A1 | 2/2017 | |
| WO | 2017117473 | A1 | 7/2017 | |
| WO | 2017117474 | A1 | 7/2017 | |
| WO | 2017161119 | A1 | 9/2017 | |
| WO | 2017176957 | A1 | 10/2017 | |
| WO | 2017176958 | A1 | 10/2017 | |
| WO | 2017184589 | A1 | 10/2017 | |
| WO | 2017185023 | A1 | 10/2017 | |
| WO | 2017185031 | A1 | 10/2017 | |
| WO | 2017185034 | A1 | 10/2017 | |
| WO | 2017185036 | A1 | 10/2017 | |
| WO | 2017197046 | A1 | 11/2017 | |
| WO | 2017197055 | A1 | 11/2017 | |
| WO | 2017197056 | A1 | 11/2017 | |
| WO | 2017223415 | A1 | 12/2017 | |
| WO | 2017223452 | A1 | 12/2017 | |
| WO | 2018052945 | A1 | 3/2018 | |
| WO | 2018052949 | A1 | 3/2018 | |
| WO | 2018064589 | A1 | 4/2018 | |
| WO | 2018071606 | A1 | 4/2018 | |
| WO | WO 2020/023782 | A1 * | 1/2020 | ........... C07D 401/14 |
| WO | 2020118098 | A1 | 6/2020 | |

OTHER PUBLICATIONS

Dharmaiah et al., "Structural basis of recognition of farnesylated and methylated KRAS4b by PDEδ," Proc. Natl. Acad. Sci. U.S.A. 2016, 113, E6766-E6775.
Elyada et al., "CK1α ablation highlights a critical role for p53 in invasiveness control," Nature 2011, 470, 409-13.
Frett et al., "Targeting the K-Ras/PDEδ protein-protein interaction: the solution for Ras-driven cancers of just another therapeutic mirage?" ChemMedChem 2013, 8, 1620-2.
Hondowicz et al., "Interieukin-2-dependent allergen-specific tissue-resident memory cells drive asthma," Immunity 2016, 44, 155-66.
Knippschild et al., "The CK1 family: contribution to cellular stress response and its role in carcinogenesis," Front. Oncol. 2014, 4, Article 96.
Levine et al., "The first 30 years of p53: growing ever more complex," Nat. Rev. Cancer 2009, 9, 749-58.
Matek and Castro, "Interleukin-2 receptor signaling: at the interface between tolerance and immunity," Immunity 2010, 32, 153-65.
Norton et al., "Evaluation of the 17-kDa prenyl-binding protein as a regulatory protein for phototransduction in retinal photoreceptors," J Biol. Chem. 2005, 280, 1248-56.
Ruchelman et al., "Isosteric analogs of lenalidomide and pomalidomide: synthesis and biological activity," Bioorg. Med. Chem. Lett. 2012, 23, 360-5.
Schittek and Sinnberg, "Biological functions of casein kinase 1 isoforms and putative roles in tumorigenesis," Mol. Cancer 2014, 13, Article 231.
Schmick et al., "Ras moves to stay In place," Trends Cell Biol. 2015, 25, 190-7.
Schneider et al., "Role of casein kinase 1A1 in the biology and targeted therapy of del(5q) MDS," Cancer Cell 2014, 26, 509-20.
Spiegel et al., "Small-molecule modulation of Ras signaling," Nat. Chem. Biol. 2014, 10, 613-22.
Stewart et al., "New thalidomide analogues derived through Sonogashira or Suzuki reactions and their TNF expression inhibition profiles," Bioorg. Med. Chem. 2010, 18, 650-62.
Stewart et al., "Synthesis and TNF expression inhibitory properties of new thalidomide analogues derived via Heck cross coupling," Bioorg. Med. Chem. Lett. 2007, 17, 5819-24.
Thompson et al., "In vitro approach to assess the potential for risk of idiosyncratic adverse reactions caused by candidate drugs," Chem. Res. Toxicol. 2012, 25, 1616-32.
Wilson et al., "Small-molecule inhibitors of IL-2/IL-2R: lessons learned and applied," Curr. Top. Microbiol. Immunol. 2011, 348, 25-59.
Zhang et al., Functional Study of Photoreceptor PDEδ in Retinal Degenerative Diseases in Advances in Experimental Medicine and Biology; Hollyfield et al., Eds.; Springer, Boston, MA, 2006; vol. 572, pp. 485-490.
Zimmerman et al., "Small molecule inhibition of the KRAS-PDEδ interaction impairs oncogenic KRAS signaling," Nature 2013, 497, 638-42.
Huart et al., "CK1α plays a central role in mediating MDM2 control of p53 and E2F-1 protein stability," J. Biol. Chem. 2009, 284, 32384-94.

* cited by examiner

SUBSTITUTED ISOINDOLINONES

CROSS REFERENCE TO RELATED APPLICATIONS

This application is a continuation of U.S. application Ser. No. 16/681,180, filed Nov. 12, 2019; which claims the benefit of priority to U.S. Provisional Application No. 62/760,813, filed Nov. 13, 2018; the disclosure of each of which is incorporated herein by reference in its entirety.

BACKGROUND

Field

Substituted isoindolinones, methods of making such compounds, pharmaceutical compositions and medicaments comprising such compounds, and their uses to treat or ameliorate diseases, disorders, or conditions associated with protein malfunction are provided.

Description of the Related Technology

Aberrant protein function, and/or protein imbalance is a hallmark of many disease states. For example, protein synthesis, cell growth, and cell proliferation are each strictly regulated processes, both spatially and temporally. Misregulation of these processes may contribute to uncontrolled cell growth, proliferation, and migration, leading to cancer.

In some instances, a protein malfunction is not a direct result of protein over- or under-expression, or alterations to the protein's sequence and structure. Rather, the malfunction may simply be the inability of a wild-type protein, with normal function and expression levels, to (for example) combat a growing tumor. For example, phosphodiesterase 6δ (PDE6D; PDE6 delta) is an important factor in KRas-driven cancers. PDE6 is crucial for maintaining high levels of KRas in the plasma membrane, where it exerts its effects on oncogenic signal transduction. PDE6 is also involved in phototransduction in retinal photoreceptors. See, e.g., Norton, et al., *J. Biol. Chem., Vol.* 280, No. 2, pp. 1248-1256 (2005). Photoreceptors absorb photons of light, which activate opsins, results in GDP/GTP exchange on transducin. This activates PDE6, which then degrades cytosolic cGMP, resulting in cellular hyperpolarization and visual signal transduction. Defects in PDE6 are also associated with various retinal disorders, including retinitis pigmentosa, diabetic retinopathy, and age-related macular degeneration. PDE6δ is also involved in ciliopathies such as Joubert syndrome.

In some instances, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha, or TNF-α) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, endotoxin shock, osteoporosis, neurodegenerative diseases (such as multiple sclerosis, Alzheimer's disease, Parkinson's disease), congestive heart failure, and psoriasis among others.

Recent data from clinical trials support the use of protein antagonists of cytokines, for example soluble TNF-α receptor fusion protein (etanercept) or the monoclonal TNF-α antibody (infliximab), for the treatment of rheumatoid arthritis, Crohn's disease, juvenile chronic arthritis and psoriatic arthritis. Thus, the reduction of pro-inflammatory cytokines such as TNF-α and interleukin-1 (IL-I) has become an accepted therapeutic approach for potential drug intervention in these conditions.

IL-2 is a cytokine produced primarily by CD4+ T cells following antigen stimulation but also produced to a lesser extent by CD8+ cells, NK T cells, activated dendritic cells (DCs), and mast cells. IL-2, the first interleukin peptide hormone discovered, is characterized by its ability to stimulate T-cell proliferation. Mature IL-2, a secreted glycoprotein of 133 amino acids (15.5 kDa), is a single chain polypeptide produced by T cells in response to immune stimuli mediated by the T-cell receptor (TCR) and major histocompatibility complexes (MHC) I and II. In the resting immune system of healthy individuals, circulating IL-2 levels are extremely low or undetectable, while raised levels follow infection and accompany normal immune response.

The IL-2 receptor family comprises three single-pass transmembrane proteins, IL-2Rα (p55, CD25), IL-2Rβ (p75, CD122), and IL-2Rγ (p64, CD132). IL-2Rα is present at low concentrations on T cells and is expressed along with IL-2 following TCR activation. IL-2Ra antagonists have been considered as agents for restricting the immune response, since IL-2Ra is strongly upregulated during the immune response and establishes the IL-2-selective high-affinity receptor complex (Malek et al., Immunity, 2010; 32(2):153-165). Both therapeutic antibody and small-molecule discovery programs have sought to develop IL-2Ra-selective inhibitors. Anti-IL-2α treatment has found an FDA-approved home in allograft transplantation to promote graft survival and is being explored in chronic inflammation as well autoimmune diseases (Wilson et al., Curr Top Microbiol Immunol. 2011; 348:25-59). This underscores the need for discovery of IL-2 inhibitors. IL-2 dependent CD4+ resident memory Th2 cells act as promoters of allergic diseases, highlighting the therapeutic potential of targeting IL-2 in allergic diseases (Hondowicz et al., Immunity, 2016; 44(1)155-166).

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including casein kinase 1α (CK1α), and the zinc-finger transcription factors aiolos, helios, and ikaros. Aiolos, helios, and ikaros are transcription factors whose expression is restricted to lymphoid lineages. Expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

Casein kinase 1α (CK1α) phosphorylates key regulatory molecules involved in the cell cycle, transcription and translation, cytoskeleton, cell-cell adhesion and signal transduction. As such, CK1α is a significant factor in the progression of a wide variety of tumors. See, e.g., Schittek and Sinnberg, *Mol. Cancer*, Vol. 13, pp. 13-26 (2014) and Krippschild, et al., *Front. Oncol.*, Vol. 4, Article 96, pp. 1-32 (2014). For example, CK1α is a critical component of the β-catenin-degradation complex and a critical regulator of the Wnt signaling pathway, and its ablation induces both Wnt and p53 activation. Schittek and Sinnberg, *Mol. Cancer.*, Vol. 13, p. 231 (2014); Cheong and Virshup, *J. Biochem. Cell Biol.* 2011, 43, 465-469; Elyada et al., *Nature*, Vol. 470, pp. 409-413 (2011). CK1α phosphorylates β-catenin, which is subsequently further phosphorylated by GSK-3β. This destabilizes β-catenin and marks the protein for ubiquitination and proteosomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758. CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53.

The primary strategy to combat uncontrolled cell growth is by administration of cytotoxic compounds that preferentially kill diseased cells, but can also be extremely toxic to normal, healthy, cells. Indeed, toxicity is a leading cause of attrition of drug candidates during the all phases of pharmaceutical research and development. See, e.g., Thompson, et al., *Chem. Res. Tox.*, Vol. 25, No. 8, pp. 1616-1632 (2012). In the last decade, large molecule antibody therapeutics have also been used to treat proliferative disorders such as cancer. However, these agents suffer from delivery, dosing, toxicity, and degradation issues. Accordingly, compounds that modulate protein function in target cells, without undue toxicity to unaffected cells, are necessary for the treatment and prevention of disease.

SUMMARY

The substituted isoindolindones described herein have been discovered to exert surprising and unexpected biological effects. For example, the compounds disclosed in the present application selectively modulate protein activity and/or protein levels to restore protein homeostasis while minimizing toxicity to healthy cells.

Some embodiments provide a compound of Formula (I):

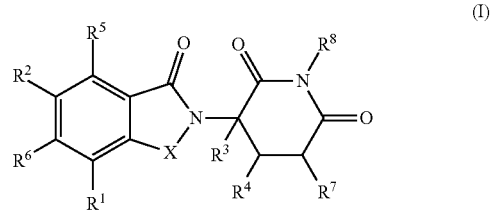

or a pharmaceutically acceptable salt thereof, wherein:

X is $CH_2$ or $C=O$;

$R^1$ is $C_3$-$C_8$ cycloalkyl, $C_4$-$C_8$ cycloalkenyl, or 3 to 10 membered heterocyclyl, each optionally substituted with one or more $R^A$, or $C_1$-$C_6$ alkyl substituted with one or more $R^A$;

each of $R^2$, $R^5$ and $R^6$ is independently hydrogen, deuterium, halogen, hydroxy, cyano, nitro, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, optionally substituted amino, optionally substituted C-amido, optionally substituted N-amido, optionally substituted N-sulfonamido, optionally substituted S-sulfoamido, $C_1$-$C_6$ alkylamino, (amino)$C_1$-$C_6$ alkyl, ($C_1$-$C_6$ alkoxy)$C_1$-$C_6$ alkyl, —O—($C_1$-$C_6$ alkoxy)$C_1$-$C_6$ alkyl, optionally substituted $C_3$-$C_8$ cycloalkyl, or optionally substituted $C_4$-$C_8$ cycloalkenyl;

$R^3$ is hydrogen, deuterium, halogen, or $C_1$-$C_6$ alkyl;

each $R^4$ and $R^7$ is independently hydrogen or $C_1$-$C_6$ alkyl;

$R^8$ is H, deuterium, $C_1$-$C_6$ alkyl,

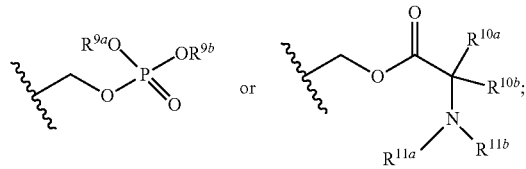

each $R^A$ is independently deuterium, hydroxy, halogen, cyano, nitro, optionally substituted $C_1$-$C_6$alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C=O)NR$^{12a}$R$^{12b}$, —NR$^{12a}$(C=O)($C_1$-$C_6$ alkyl), ($C_1$-$C_6$ alkoxy)$C_1$-$C_6$ alkyl, —O—($C_1$-$C_6$ alkoxy)$C_1$-$C_6$ alkyl, optionally substituted $C_3$-$C_8$ cycloalkyl, optionally substituted $C_4$-$C_8$ cycloalkenyl, or optionally substituted 3 to 7 membered heterocyclyl; or two geminal $R^A$ form oxo;

each of $R^{9a}$ and $R^{9b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{10a}$ and $R^{10b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{11a}$ and $R^{11b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{12a}$ and $R^{12b}$ is independently H or $C_1$-$C_6$ alkyl, or $R^{12a}$ and $R^{12b}$ together with the nitrogen atom to which they are attached form an optionally substituted 5 or 6 membered heterocyclyl optionally substituted with one or more $R^{13}$; and each $R^{13}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{13}$ form oxo. In some embodiments, when $R^1$ is optionally substituted 3 to 10 membered heterocyclyl, and each of $R^3$, $R^4$, $R^7$ and $R^8$ is hydrogen; then at least one of $R^2$, $R^5$ and $R^6$ is not hydrogen. In some embodiments, when $R^1$ is trifluoromethyl, and each of $R^3$, $R^4$, $R^7$ and $R^8$ is hydrogen; then $R^2$ is halogen.

In some embodiments, the compound of Formula (I) is also represented for Formula (Ia):

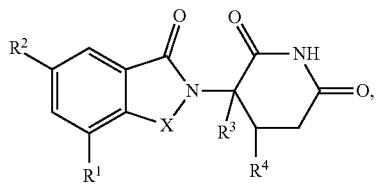

or a pharmaceutically acceptable salt thereof. In some other embodiments, the compound of Formula (I) is also represented for Formula (Ib)

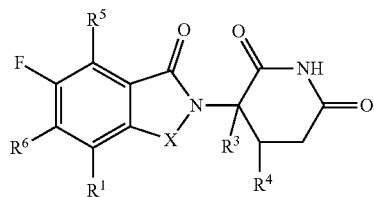

or Formula (Ic)

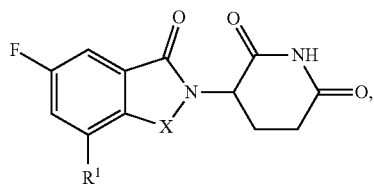

or a pharmaceutically acceptable salt thereof.

Some embodiments of the present disclosure provide a pharmaceutical composition comprising a compound of Formula (I), (Ia), (Ib) or (Ic), or a pharmaceutically acceptable salt thereof, and at least one pharmaceutically acceptable excipient or carrier.

Some embodiments provide a method of treating or ameliorating cancer in a subject in need thereof, comprising administering a therapeutically effective amount of a compound of Formula (I), (Ia), (Ib) or (Ic), or a pharmaceutically acceptable salt thereof, or a pharmaceutical composition thereof, to the subject. Other embodiments provide a method of treating or ameliorating a retinal disease in a subject in need thereof, comprising administering a therapeutically effective amount of a compound of Formula (I), (Ia), (Ib) or (Ic), or a pharmaceutically acceptable salt thereof, or a pharmaceutical composition thereof, to the subject. Other embodiments provide a method of treating or ameliorating or ameliorating an inflammatory disease, an autoimmune disease, an allergic disease, or a neurodegenerative disease in a subject in need thereof, comprising administering a therapeutically effective amount of a compound of Formula (I), (Ia), (Ib) or (Ic), or a pharmaceutically acceptable salt thereof, or a pharmaceutical composition thereof, to the subject.

Additional embodiments provide a method of inhibiting protein activity in one or more cells of a biological sample, comprising contacting a compound of Formula (I), (Ia), (Ib) or (Ic), or a pharmaceutically acceptable salt thereof with the cells in the biological sample. The protein may be CK1α, PDE6, or ikaros, or combinations thereof. Further embodiments provides a method of treating or ameliorating a disease, disorder or condition mediated by CK1α, ikaros, or PDE6, comprising administering a therapeutically effective amount of a compound of Formula (I), (Ia), (Ib) or (Ic), or a pharmaceutically acceptable salt thereof, or a pharmaceutical composition thereof, to a subject in need thereof.

Further embodiments provide a method of modulating cytokine activity in one or more cells of a biological sample, comprising contacting a compound of Formula (I), (Ia), (Ib) or (Ic), or a pharmaceutically acceptable salt thereof with the cells in the biological sample. In some embodiments, the cytokine is TNFα, IL-1β, IL-2, or IL-6, or combinations thereof. Further embodiments provides a method of treating or ameliorating a disease, disorder or condition mediated by one or more cytokines described herein, comprising administering a therapeutically effective amount of a compound of Formula (I), (Ia), (Ib) or (Ic), or a pharmaceutically acceptable salt thereof, or a pharmaceutical composition thereof, to a subject in need thereof.

DETAILED DESCRIPTION

Disclosed herein are compounds useful for the treatment or amelioration of various diseases, disorders, or conditions associated with protein malfunctions, including various types of cancers. In some aspects, these compounds are inhibitors of one or more cytokines, PDE6, ikaros, or CK1α.

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, common organic abbreviations are defined as follows:

ACN acetonitrile
AcOH acetic acid
CCL$_4$ carbon tetrachloride
CDI 1,1'-carbonyldiimidazole, N,N-carbonyldiimidazole
d day, days
DCM dichloromethane, methylene chloride
DEAD diethyl azodicarboxylate
DIEA N,N-diisopropylethylamine
DMA N,N-dimethylamide
DMF N,N-dimethylformamide
DMSO dimethylsulfoxide
EDAC.HCl 1-(3-dimethylaminopropyl)-3-ethylcarbodiimide hydrochloride
EDCI 1-ethyl-3-(3-dimethylaminopropyl)carbodiimide
Ether diethyl ether
EA ethyl acetate
EtOH ethanol
K$_2$CO$_3$ potassium carbonate
LiAH lithium aluminium hydride
LiCl lithium chloride
LiOH lithium hydroxide
h hour, hours
H$_2$ hydrogen
HCl hydrochloric acid, hydrochloride
HOBt 1-hydroxybenzotriazole
MeOH MeOH
m minute, minutes
NaHCO$_3$ sodium bicarbonate
Na$_2$SO$_4$ sodium sulfate
NBS N-bromosuccinimide
N$_2$ nitrogen
Pd/C palladium on activated carbon
PE petroleum ether
RT room temperature
T3P propylphosphonic anhydride
TEA triethylamine
TFA trifluoroacetic acid
THF tetrahydrofuran
quant quantitative yield As used herein, any "R" group(s) represent substituents that can be attached to the indicated atom. An R group may be substituted or unsubstituted. Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, cycloalkyl, aryl, heteroaryl, heterocyclyl, aralkyl, heteroaralkyl, heterocyclyl(alkyl), hydroxy, alkoxy, cycloalkoxy, aryloxy, acyl, mercapto, alkylthio, arylthio, cyano, halogen, C-amido, N-amido, C-carboxy, O-carboxy, isocyanato, thiocyanato, isothiocyanato, nitro, haloalkyl, haloalkoxy, amino (including mono-substituted amino and di-substituted amino), and alkylamino. When a group is not described as "optionally substituted," "unsubstituted" or "substituted," such group is unsubstituted unless the definition of such group states otherwise.

As used herein, "C$_a$ to C$_b$" in which "a" and "b" are integers refer to the number of carbon atoms in an alkyl, alkenyl or alkynyl group, or the number of carbon atoms in the ring of a cycloalkyl, aryl, heteroaryl or heterocyclyl group. That is, the alkyl, alkenyl, alkynyl, ring of the cycloalkyl, ring of the aryl, ring of the heteroaryl or ring of the heterocyclyl can contain from "a" to "b", inclusive, carbon atoms. Thus, for example, a "C$_1$ to C$_4$ alkyl" group or a "C$_1$-C$_4$ alkyl" group refers to all alkyl groups having from 1 to 4 carbons, that is, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—. Likewise, for example, cycloalkyl group may contain from "a" to "b", inclusive, total atoms, such as a C$_3$-C$_8$ cycloalkyl group, 3 to 8 carbon atoms in the ring(s). If no "a" and "b" are designated with regard to an alkyl, cycloalkyl, or cycloalkenyl, the broadest range described in these definitions is to be assumed. Similarly, a "4 to 7 membered heterocyclyl" group refers to all heterocyclyl groups with 4 to 7 total ring atoms, for example, azetidine, oxetane, oxazoline, pyrrolidine, piperidine, piperazine, morpholine, and the like. As used herein, the term "$C_1$-$C_6$" includes $C_1$, $C_2$, $C_3$, $C_4$, $C_5$ and $C_6$, and a range defined by any of the two preceding numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl. As another example, 3 to 10 membered heterocyclyl includes 3, 4, 5, 6, 7, 8, 9, or 10 ring atoms, or a range defined by any of the two preceding numbers, such as 4 to 6 membered or 5 to 7 membered heterocyclyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, isopropyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl, and hexyls.

As used herein, the term "alkenyl" refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

As used herein, the term "alkynyl" refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a bridged, fused, or spiro fashion. Cycloalkyl groups can contain 3 to 10 atoms in the ring(s) or 3 to 8 atoms in the ring(s). Typical cycloalkyl groups include, but are in no way limited to, cyclopropyl, cyclobutyl, cyclopentyl, cyclohexyl, cycloheptyl, cyclooctyl, norbornyl, decalinyl, bicyclo[2.2.1]heptane, bicyclo[2.2.2]octane and spiro[3.5]nonyl.

As used herein, "cycloalkene" or "cycloalkenyl" refers to a partially saturated mono- or multi-cyclic hydrocarbon ring system, that is, having one or more double bonds, situated in such a way, however, that a fully delocalized pi-electron system does not occur throughout all the ring(s). When composed of two or more rings, the rings may be joined together in a bridged, fused, or spiro fashion. Cycloalkenyl groups can contain 4 to 10 atoms in the rings(s) or 5 to 10 atoms in the ring(s). Typical cycloalkenyl groups include, but are in no way limited to, cyclopentenyl, cyclohexenyl, cycloheptenyl, and cyclooctenyl.

As used herein, "alkoxy" refers to the formula —OR wherein R is an alkyl as defined above. A non-limiting list of alkoxys is methoxy, ethoxy, n-propoxy, n-butoxy, isobutoxy, sec-butoxy, and tert-butoxy.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl.

As used herein, "haloalkoxy" refers to an alkoxy group defined herein in which one or more of the hydrogen atoms are replaced by a halogen (for example, mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy.

As used herein, the term "halogen atom" or "halogen" means any one of the radio-stable atoms of column 7 of the Periodic Table of the Elements, such as, fluorine, chlorine, bromine, and iodine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidone, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "lower alkylene groups" are straight-chained —CH$_2$— tethering groups, forming bonds to connect molecular fragments via their terminal carbon atoms. Lower alkylene groups contain from 1 to 6 carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—).

As used herein, "aralkyl" and "aryl(alkyl)" refer to an aryl group, as defined above, connected, as a substituent, via a lower alkylene group, as described above. The lower alkylene and aryl group of an aralkyl may be substituted or unsubstituted.

As used herein, "heteroaralkyl" and "heteroaryl(alkyl)" refer to an heteroaryl group, as defined above, connected, as a substituent, via a lower alkylene group, as described above. The lower alkylene and heteroaryl group of a heteroaralkyl may be substituted or unsubstituted.

As used herein, "heterocyclylalkyl" and "heterocyclyl(alkyl)" refer to a heterocyclyl group (as defined herein) connected, as a substituent, via a lower alkylene group. The lower alkylene and heterocyclyl group of an heterocyclylalkyl may be substituted or unsubstituted.

The term "amino" refers to a —NH$_2$ group. The term "optionally substituted amino," as used herein refer to a —NR$_A$R$_B$ radical where R$_A$ and R$_B$ are independently hydrogen, alkyl, cycloalkyl, aryl, heteroaryl, heterocyclyl, aralkyl, heteroaryl(alkyl), or heterocyclyl(alkyl), as defined herein and at least one of R$_A$ and R$_B$ is not hydrogen.

As used herein, "alkylamino" or "(alkyl)amino" refers to a —NR$_A$R$_B$ group where R$_A$ and R$_B$ are hydrogen or alkyl as defined above, and at least one of R$_A$ and R$_B$ is alkyl. The alkyl portion of the (alkyl)amine, includes, for example, C$_1$-C$_6$ alkyl groups. Examples of alkylamino groups include, but are not limited to methylamino (—NHMe), ethylamino (—NHEt), dimethylamino (—N(Me)$_2$, methylethylamino (—N(Me)(Et)), and isopropylamino (—NHiPr).

As used herein, "aminoalkyl" or "amino(alkyl)" refers to an alkyl group in which one or more of the hydrogen atoms are replaced by an amino group or "—NR$_A$R$_B$" group as defined herein. The alkyl portion of the amino(alkyl), includes, for example, C$_1$-C$_6$ alkyl. Examples of aminoalkyl groups include, but are not limited to —(CH$_2$)$_{1-4}$NH$_2$, —(CH$_2$)$_{1-4}$—NHCH$_3$, —(CH$_2$)$_{1-4}$—NHC$_2$H$_5$, —(CH$_2$)$_{1-4}$—N(CH$_3$)$_2$, —(CH$_2$)$_{1-4}$—N(C$_2$H$_5$)$_2$, —(CH$_2$)$_{1-4}$—NH—CH(CH$_3$)$_2$, —(CH$_2$)$_{1-4}$ N(CH$_3$)C$_2$H$_5$, and —CH(NH$_2$)CH$_3$.

As used herein, "alkoxyalkyl" or "(alkoxy)alkyl" refers to an alkoxy group connected via an lower alkylene group, such as C$_2$-C$_8$ alkoxyalkyl, or (C$_1$-C$_6$ alkoxy)C$_1$-C$_6$ alkyl, for example, —(CH$_2$)$_{1-3}$—OCH$_3$.

As used herein, "—O-alkoxyalkyl" or "—O—(alkoxy)alkyl" refers to an alkoxy group connected via an —O—(lower alkylene) group, such as —O—(C$_1$-C$_6$ alkoxy)C$_1$-C$_6$ alkyl, for example, —O—(CH$_2$)$_{1-3}$—OCH$_3$.

A "hydroxy" group refers to a —OH group.

A "cyano" group refers to a "—CN" group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, heteroaryl(alkyl), or heterocyclyl(alkyl), as defined above. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, heteroaryl(alkyl), or heterocyclyl(alkyl), as defined above. An N-sulfonamido may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, heteroaryl(alkyl), or heterocyclyl(alkyl), as defined above. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, heteroaryl(alkyl), or heterocyclyl(alkyl), as defined above. An N-amido may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, aralkyl, heteroaryl(alkyl), or heterocyclyl(alkyl), as defined herein. An O-carboxy may be substituted or unsubstituted.

As used herein, the terms "ester" and "C-carboxy" refer to a "—C(=O)OR" group in which R can be the same as defined with respect to O-carboxy. An ester and C-carboxy may be substituted or unsubstituted.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* $3^{rd}$. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* $5^{th}$ ed., John McMurry (2000), pages 398 and 408; all of which are incorporated herein by reference for the limited purpose of disclosing characteristics and examples of leaving groups.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric and conformeric forms are also intended to be included. A conformer is a structure that is a conformational isomer. Conformational isomerism is the phenomenon of molecules with the same structural formula but different conformations (conformers) of atoms about a rotating bond.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is also understood that the compounds described herein, such as compounds of preferred embodiments, include the compound in any of the forms described herein (e.g., pharmaceutically acceptable salts, enantiomeric/diastereomeric forms, tautomeric forms, and the like).

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Compounds of Formula (I)

Some embodiments provide a compound of Formula (I):

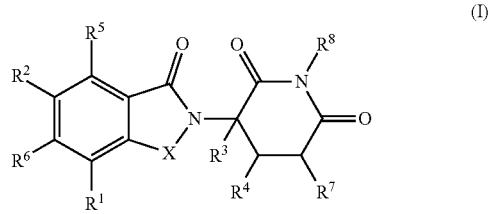

(I)

or a pharmaceutically acceptable salt thereof, wherein:

X is $CH_2$ or C=O;

$R^1$ is $C_3$-$C_8$ cycloalkyl, $C_4$-$C_8$ cycloalkenyl, or 3 to 10 membered heterocyclyl, each optionally substituted with one or more $R^A$, or $C_1$-$C_6$ alkyl substituted with one or more $R^A$;

each of $R^2$, $R^5$ and $R^6$ is independently hydrogen, deuterium, halogen, hydroxy, cyano, nitro, optionally substituted $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, optionally substituted amino, optionally substituted C-amido, optionally substituted N-amido, optionally substituted N-sulfonamido, optionally substituted S-sulfoamido, $C_1$-$C_6$ alkylamino, (amino)$C_1$-$C_6$ alkyl, ($C_1$-$C_6$ alkoxy)$C_1$-$C_6$ alkyl, —O—($C_1$-$C_6$ alkoxy)$C_1$-$C_6$ alkyl, optionally substituted $C_3$-$C_8$ cycloalkyl, or optionally substituted $C_4$-$C_8$ cycloalkenyl;

$R^3$ is hydrogen, deuterium, halogen, or $C_1$-$C_6$ alkyl;

each $R^4$ and $R^7$ is independently hydrogen or $C_1$-$C_6$ alkyl;

$R^8$ is H, deuterium, $C_1$-$C_6$ alkyl,

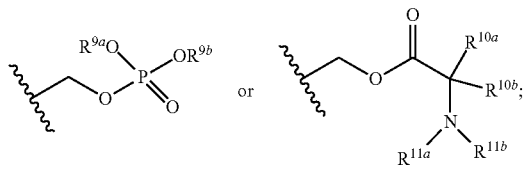

each $R^A$ is independently deuterium, hydroxy, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, (amino)$C_1$-$C_6$ alkyl, —(C=O)$NR^{12a}R^{12b}$, —$NR^{12a}$(C=O)($C_1$-$C_6$ alkyl), ($C_1$-$C_6$ alkoxy)$C_1$-$C_6$ alkyl, —O—($C_1$-$C_6$ alkoxy)$C_1$-$C_6$ alkyl, optionally substituted $C_3$-$C_8$ cycloalkyl, optionally substituted $C_4$-$C_8$ cycloalkenyl, or optionally substituted 3 to 7 membered heterocyclyl; or two geminal $R^A$ form oxo;

each of $R^{9a}$ and $R^{9b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{10a}$ and $R^{10b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{11a}$ and $R^{11b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{12a}$ and $R^{12b}$ is independently H or $C_1$-$C_6$ alkyl, or $R^{12a}$ and $R^{12b}$ together with the nitrogen atom to which they are attached form an optionally substituted 5 or 6 membered heterocyclyl optionally substituted with one or more $R^{13}$; and each $R^{13}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$alkoxy)$C_1$-$C_6$ alkyl, —O—($C_1$-$C_6$ alkoxy)$C_1$-$C_6$ alkyl, optionally substituted amino, halogen, or cyano; or two geminal $R^{13}$ form oxo. In some embodiments, when $R^1$ is optionally substituted 3 to 10 membered heterocyclyl; then at least one of $R^2$, $R^5$ and $R^6$ is not hydrogen. In some further embodiments, when $R^1$ is 3 to 10 membered heterocyclyl, and each of $R^3$, $R^4$, $R^7$ and $R^8$ is hydrogen; then at least one of $R^2$, $R^5$ and $R^6$ is not hydrogen (for example, $R^2$ is not hydrogen). In some embodiments, when $R^1$ is trifluoromethyl, each of $R^3$, $R^4$, $R^7$ and $R^8$ is hydrogen; then $R^2$ is deuterium, halogen, hydroxy, cyano, nitro, $C_1$-$C_6$ alkoxy, $C_2$-$C_6$ alkenyl, $C_2$-$C_6$ alkynyl, $C_1$-$C_6$ haloalkyl, $C_1$-$C_6$ haloalkoxy, optionally substituted amino, optionally substituted C-amido, optionally substituted N-amido, optionally substituted N-sulfonamido, optionally substituted S-sulfoamido, $C_1$-$C_6$ alkylamino, (amino)$C_1$-$C_6$ alkyl, ($C_1$-$C_6$ alkoxy)$C_1$-$C_6$ alkyl, —O—($C_1$-$C_6$ alkoxy)$C_1$-$C_6$ alkyl, optionally substituted $C_3$-$C_8$ cycloalkyl, or optionally substituted $C_4$-$C_8$ cycloalkenyl. In some further embodiments, when $R^1$ is trifluoromethyl, and each of $R^3$, $R^4$, $R^7$ and $R^8$ is hydrogen; then $R^2$ is halogen (for example, $R^2$ is fluoro). In some further embodiments, when $R^1$ is trifluoromethyl, and each of $R^3$, $R^4$, $R^7$ and $R^8$ is hydrogen; then $R^5$ is hydrogen.

In some embodiments, the compound is also represented by Formula (Ia):

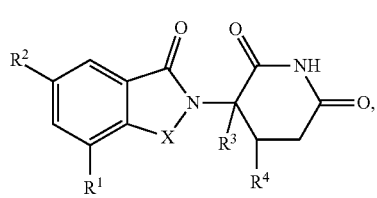

(Ia)

or a pharmaceutically acceptable salt thereof.

In some embodiments, the compound is also represented by Formula (Ib) or (Ic):

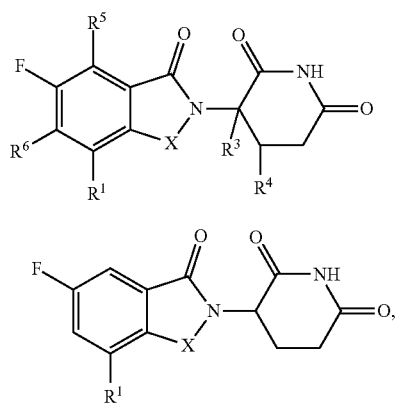

(Ib)

(Ic)

or a pharmaceutically acceptable salt thereof.

In some embodiments of the compound of Formula (I), (Ia), (Ib) or (Ic), X is $CH_2$. In other embodiments, X is C═O.

In some embodiments of the compound of Formula (I), (Ia), (Ib) or (Ic), $R^1$ is an optionally substituted $C_3$-$C_8$ cycloalkyl, such as cyclopropyl, cyclobutyl, cyclopentyl, cyclohexyl, cycloheptyl, bicycloheptyl or cyclooctyl. In other embodiments, $R^1$ is optionally substituted $C_4$-$C_8$ cycloalkenyl, such as cyclopent-1-ene, cyclopent-2-ene, cyclohex-1-ene, cyclohex-2-ene, cyclohex-3-ene, cyclohept-1-ene, cyclohept-2-ene, cyclohept-3-ene, cyclohept-4-ene, cyclooct-1-ene, cyclooct-2-ene, cyclooct-3-ene, or cyclooct-4-ene. In some further embodiments, $R^1$ is cyclopropyl, cyclobutyl, cyclohexyl, cyclopentyl, cycloheptyl, bicyclo[2.2.1]heptyl

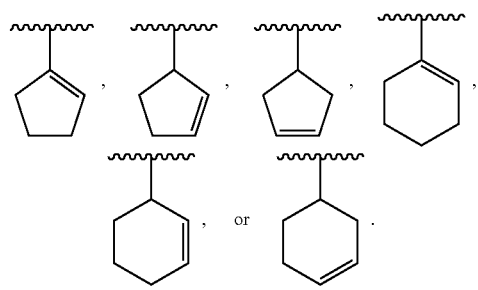

In some such embodiments, $R^1$ is unsubstituted. In other embodiments, $R^1$ is substituted with one or more $R^A$. In some such embodiments, $R^1$ is substituted with one $R^A$. In some other embodiments, $R^1$ is substituted with two $R^A$. In some such embodiments, each $R^A$ is independently selected from the group consisting of halogen (e.g., chloro or fluoro), $C_1$-$C_6$ alkyl (e.g., methyl, ethyl, isopropyl, or t-butyl), $C_1$-$C_6$ haloalkyl (e.g., trifluoromethyl), and $C_3$-$C_7$ cycloalkyl (e.g., cyclopropyl) optionally substituted with one or more halogen, $C_1$-$C_6$ alkyl, $C_1$-$C_6$ alkoxy, $C_1$-$C_6$ haloalkyl, or $C_1$-$C_6$ haloalkoxy, or combinations thereof. In some further embodiments, $R^1$ is

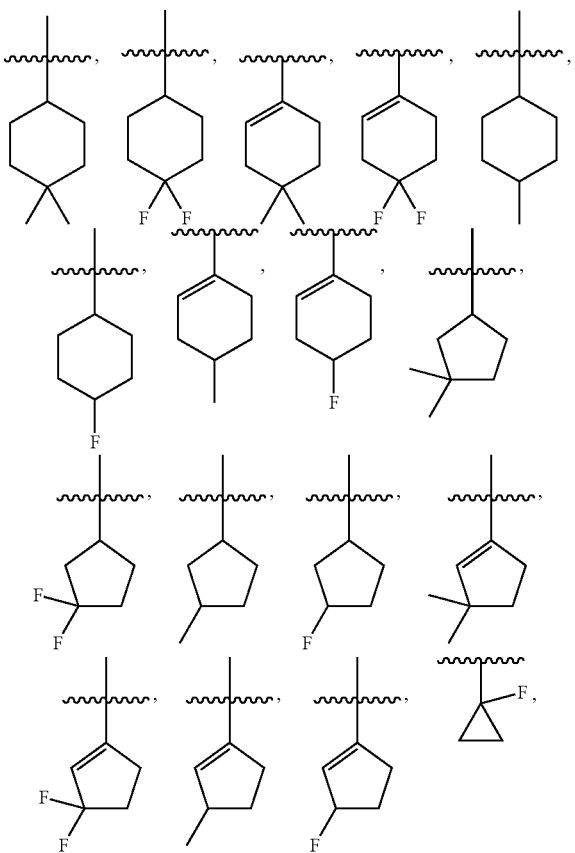

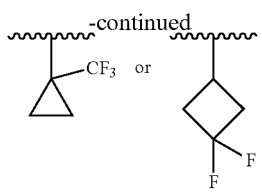

In additional embodiments the compound of Formula (I), (Ia), (Ib) or (Ic), $R^1$ is $C_1$-$C_6$ alkyl substituted with one or more $R^A$. In some such embodiments, $R^1$ is $C_1$-$C_3$ alkyl or $C_2$-$C_4$ alkyl (e.g., ethyl, propyl, isopropyl, n-butyl, isobutyl, or t-butyl) substituted with one or two $R^A$ independently selected from the group consisting of halogen (e.g., chloro or fluoro), $C_1$-$C_6$ alkyl (e.g., methyl, ethyl, isopropyl, or t-butyl), $C_1$-$C_6$ haloalkyl (e.g., trifluoromethyl), and $C_3$-$C_7$ cycloalkyl (e.g., cyclopropyl) optionally substituted with one or more halogen, $C_1$-$C_6$ alkyl, $C_1$-$C_6$ alkoxy, $C_1$-$C_6$ haloalkyl, or $C_1$-$C_6$ haloalkoxy, or combinations thereof. In some further embodiments, $R^1$ is —$CH_2F$, —$CHF_2$, —$CH_2CH_2F$, —$CH_2CHF_2$, —$CH(CH_3)CF_3$ or —CH($CH_2CH_3$)$CF_3$. In some embodiments, $R^1$ is not —$CF_3$. In other embodiments, when $R^1$ is —$CF_3$, then $R^2$ is halogen (e.g., fluoro), hydroxy, cyano, nitro, $C_1$-$C_6$ alkoxy (such as methoxy), $C_2$-$C_6$ alkenyl, $C_2$-$C_6$ alkynyl, $C_1$-$C_6$ haloalkyl (such as trifluoromethyl), or $C_1$-$C_6$ haloalkoxy (such as trifluoromethoxy).

In additional embodiments the compound of Formula (I), (Ia), (Ib) or (Ic), $R^1$ is optionally substituted 3 to 7 membered heterocyclyl. In some such embodiments, the heterocyclyl group contains one or more heteroatoms selected from the group consisting of nitrogen, oxygen, sulfur, and combinations thereof. In other embodiments, the heterocyclyl group contains one unsaturated bond (e.g., one carbon-carbon double bond) within the ring or ring system. In some embodiments of the compound where $R^1$ is an optionally substituted heterocyclyl group, $R^2$ is not hydrogen. In some such embodiments, $R^2$ is halogen (such as fluoro or chloro), hydroxy, cyano, nitro, $C_1$-$C_6$ alkyl (such as methyl), $C_1$-$C_6$ alkoxy (such as methoxy), $C_2$-$C_6$ alkenyl, $C_2$-$C_6$ alkynyl, $C_1$-$C_6$ haloalkyl (such as trifluoromethyl), $C_1$-$C_6$ haloalkoxy (such as trifluoromethoxy), optionally substituted (for example, when $R^2$ is optionally substituted $C_3$-$C_8$ cycloalkyl or optionally substituted $C_4$-$C_8$ cycloalkenyl).

In some embodiments the compound of Formula (I) or (Ia), $R^2$ is hydrogen. In other embodiments, $R^2$ is deuterium. In still other embodiments, $R^2$ is halogen, such as fluoro or chloro. In some embodiments, $R^2$ is $C_1$-$C_6$ alkyl, such as methyl, ethyl, n-propyl, iso-propyl, n-butyl, sec-butyl, t-butyl, pentyl (straight chain or branched), or hexyl (straight chain or branched). In other embodiments, $R^2$ is $C_1$-$C_6$ alkoxy, such as methoxy, ethoxy, n-propoxy, iso-propoxy, n-butoxy, sec-butoxy, t-butoxy, pentoxy (straight chain or branched), or hexoxy (straight chain or branched). In still other embodiments, $R^2$ is $C_1$-$C_3$ haloalkyl, such as $C_1$-$C_3$ fluoroalkyl or $C_1$-$C_3$ chloroalkyl. For example, $R^2$ can be —$CH_2F$, —$CHF_2$, —$CF_3$, —$CH_2CF_3$, —$CF_2CF_3$, —(CH)$CH_3CF_3$, or —$CH_2C_1$. In some embodiments, $R^2$ is hydrogen, fluoro, chloro, methyl, trifluoromethyl, or methoxy. In some embodiments, $R^2$ is not hydrogen. In some embodiments, when $R^2$ is optionally substituted (for example, when $R^2$ is optionally substituted $C_3$-$C_8$ cycloalkyl or optionally substituted $C_4$-$C_8$ cycloalkenyl), $R^2$ is optionally substituted with one or more $R^A$.

In some embodiments of the compound of Formula (I), (Ia) or (Ib), $R^3$ is hydrogen. In other embodiments, $R^3$ is deuterium. In still other embodiments, $R^3$ is fluoro. In yet other embodiments, $R^3$ is methyl or ethyl. In some embodiments, $R^3$ is not hydrogen.

In some embodiments the compound of Formula (I), (Ia) or (Ib), $R^4$ is hydrogen. In other embodiments, $R^4$ is $C_1$-$C_6$ alkyl, for example, methyl. In some embodiments, $R^4$ is not hydrogen.

In some embodiments the compound of Formula (I) or (Ib), $R^5$ is hydrogen, deuterium, halogen, $C_1$-$C_6$ alkyl, $C_1$-$C_6$ alkoxy, or $C_1$-$C_3$ haloalkyl. In some further embodiments, $R^5$ is hydrogen, fluoro, chloro, methyl, trifluoromethyl, or methoxy. In one embodiment, $R^5$ is hydrogen. In another embodiment, $R^5$ is fluoro. In some embodiments, when $R^5$ is optionally substituted (for example, when $R^5$ is optionally substituted $C_3$-$C_8$ cycloalkyl or optionally substituted $C_4$-$C_8$ cycloalkenyl), $R^5$ is optionally substituted with one or more $R^A$.

In some embodiments the compound of Formula (I) or (Tb), $R^6$ is hydrogen. In other embodiments, $R^6$ is deuterium. In still other embodiments, $R^6$ is halogen, such as fluoro or chloro. In some embodiments, $R^6$ is $C_1$-$C_6$ alkyl, such as methyl, ethyl, n-propyl, iso-propyl, n-butyl, sec-butyl, t-butyl, pentyl (straight chain or branched), or hexyl (straight chain or branched). In other embodiments, $R^6$ is $C_1$-$C_6$ alkoxy, such as methoxy, ethoxy, n-propoxy, iso-propoxy, n-butoxy, sec-butoxy, t-butoxy, pentoxy (straight chain or branched), or hexoxy (straight chain or branched). In still other embodiments, $R^6$ is $C_1$-$C_3$ haloalkyl, such as $C_1$-$C_3$ fluoroalkyl or $C_1$-$C_3$ chloroalkyl. For example, $R^6$ can be —$CH_2F$, —$CHF_2$, —$CF_3$, —$CH_2CF_3$, —$CF_2CF_3$, —(CH)$CH_3CF_3$, or —$CH_2C_1$. In some embodiments, $R^6$ is hydrogen, fluoro, methyl, trifluoromethyl, or methoxy. In some embodiments, when $R^6$ is optionally substituted (for example, when $R^6$ is optionally substituted $C_3$-$C_8$ cycloalkyl or optionally substituted $C_4$-$C_8$ cycloalkenyl), $R^6$ is optionally substituted with one or more $R^A$.

In some embodiments the compound of Formula (I), $R^7$ is hydrogen. In other embodiments, $R^7$ is $C_1$-$C_6$ alkyl (e.g., methyl).

In some embodiments the compound of Formula (I), $R^8$ is hydrogen. In other embodiments, $R^8$ is $C_1$-$C_6$ alkyl (e.g., methyl). In some embodiments, $R^8$ is

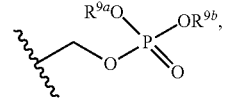

wherein each of $R^{9a}$ and $R^{9b}$ is independently H or $C_1$-$C_6$ alkyl. In one such embodiment, both $R^{9a}$ and $R^{9b}$ are t-butyl. In some embodiments, $R^8$ is

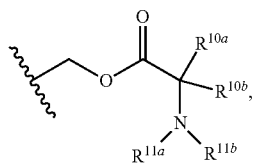

wherein each of $R^{10a}$, $R^{10b}$, $R^{11a}$ and $R^{11b}$ is independently hydrogen or $C_1$-$C_6$ alkyl. In some such embodiments, each of $R^{10a}$, $R^{11a}$ and $R^{11b}$ is hydrogen and $R^{10b}$ is $C_1$-$C_6$ alkyl (e.g., methyl, ethyl, or isopropyl).

In additional embodiments of the compound of Formula (Ia), X is $CH_2$ or C=O; $R^1$ is an unsubstituted $C_3$-$C_8$ cycloalkyl or an unsubstituted $C_4$-$C_8$ cycloalkenyl; $R^2$ is hydrogen, deuterium, halogen, an unsubstituted $C_1$-$C_6$ alkyl, an unsubstituted $C_1$-$C_6$ alkoxy, or an unsubstituted $C_1$-$C_3$ haloalkyl; $R^3$ is hydrogen, deuterium, fluoro, or methyl; $R^4$ is hydrogen or methyl; and each of $R^5$, $R^6$, $R^7$ and $R^8$ is hydrogen.

In any embodiments of the compound described herein, $R^A$ is independently halogen (e.g., chloro or fluoro), hydroxy, cyano, nitro, $C_1$-$C_6$ alkyl (e.g., methyl, ethyl, isopropyl, or t-butyl), $C_1$-$C_6$ alkoxy, $C_1$-$C_6$ haloalkyl (e.g., trifluoromethyl), $C_1$-$C_6$ haloalkoxy (e.g., trifluoromethoxy), amino, $C_1$-$C_6$ alkylamino, (amino)$C_1$-$C_6$ alkyl, or $C_3$-$C_7$ cycloalkyl (e.g., cyclopropyl) optionally substituted with one or more halogen, $C_1$-$C_6$ alkyl, $C_1$-$C_6$ alkoxy, $C_1$-$C_6$ haloalkyl, or $C_1$-$C_6$ haloalkoxy, or combinations thereof. In some further embodiments, when $R^A$ is optionally substituted $C_3$-$C_8$ cycloalkyl, optionally substituted $C_4$-$C_8$ cycloalkenyl, or optionally substituted 3 to 7 membered heterocyclyl, each of $C_3$-$C_8$ cycloalkyl, $C_4$-$C_8$ cycloalkenyl, and 3 to 7 membered heterocyclyl is either unsubstituted or substituted with one or more substituents independently selected from halogen (e.g., chloro or fluoro), $C_1$-$C_6$ alkyl (e.g., methyl, ethyl, isopropyl, or t-butyl), $C_1$-$C_6$ haloalkyl (e.g., trifluoromethyl), $C_1$-$C_6$ alkoxy (e.g., methoxy) or $C_1$-$C_6$ haloalkoxy (e.g., trifluoromethoxy).

Non-limiting exemplary compounds of Formula (I) include the following:

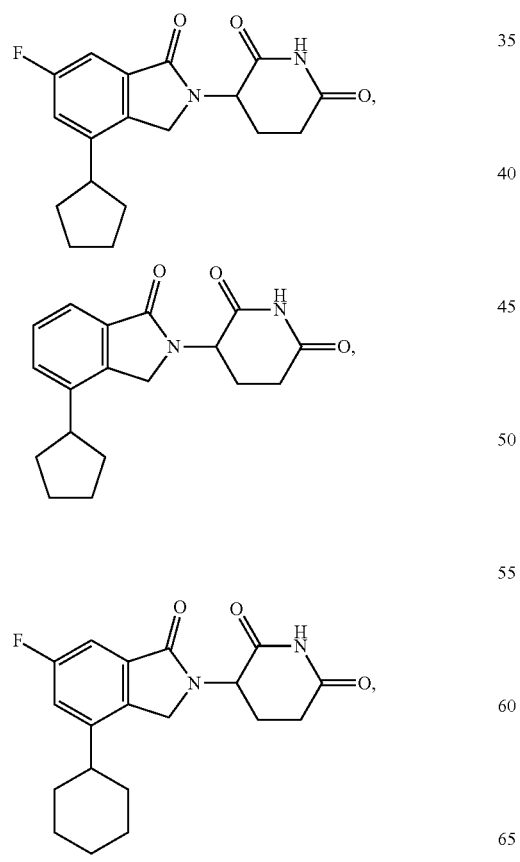

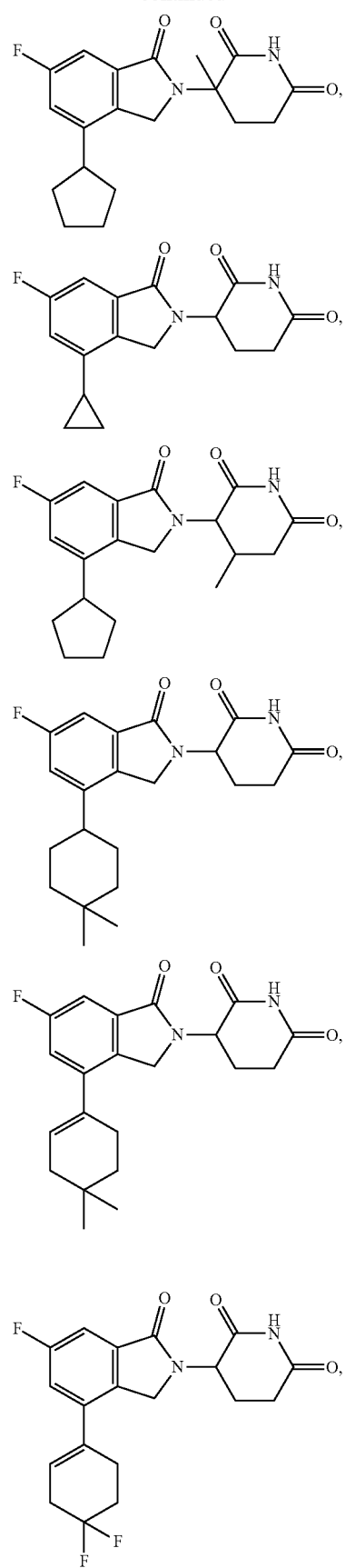

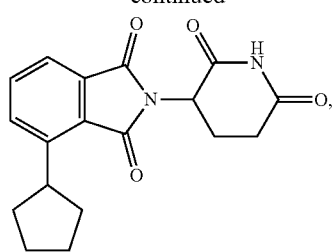
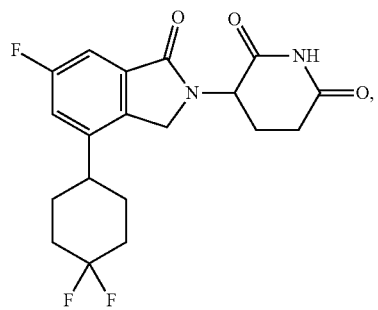
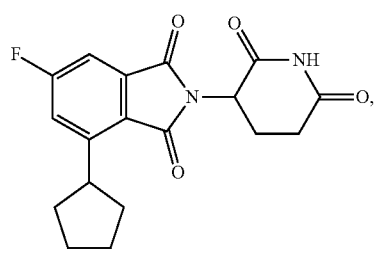
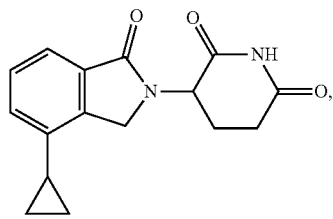
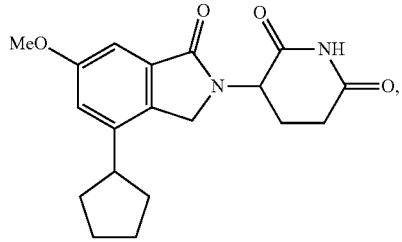
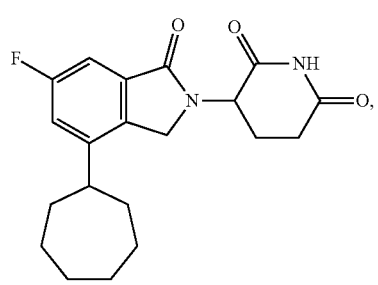
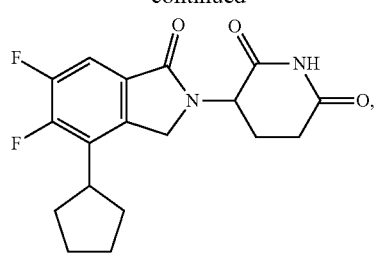
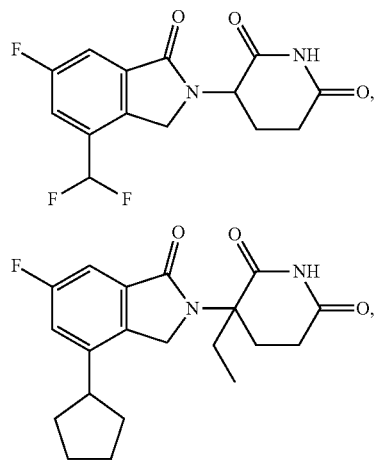
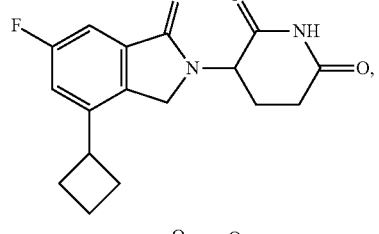
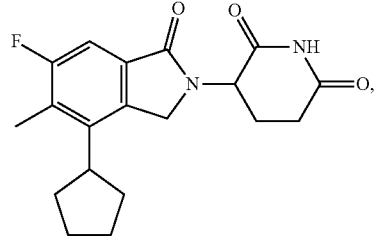
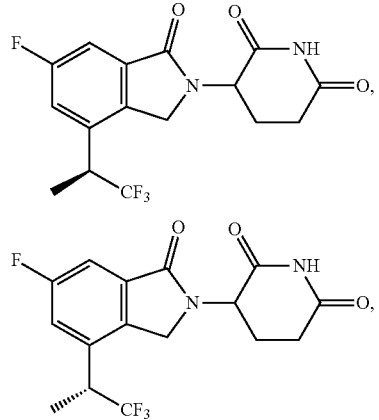

-continued

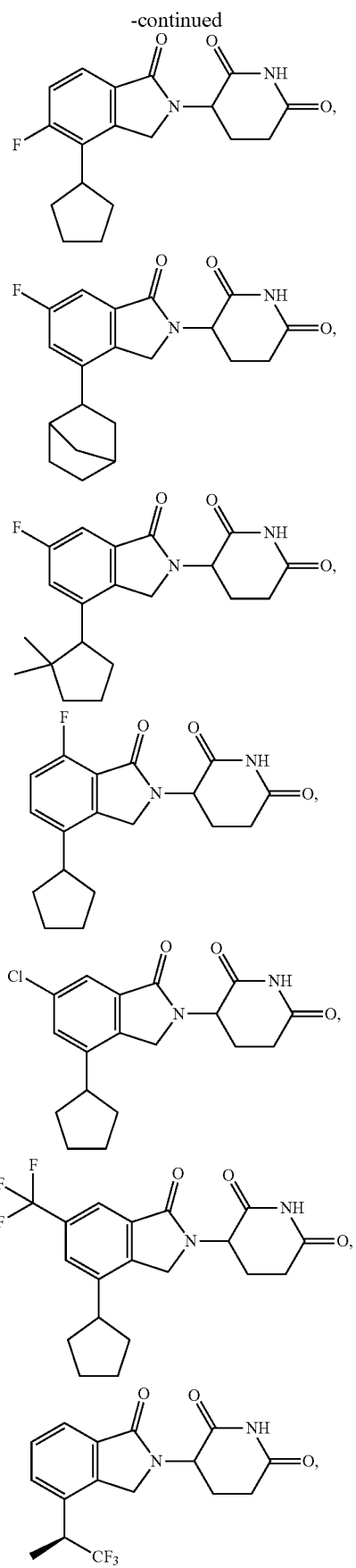

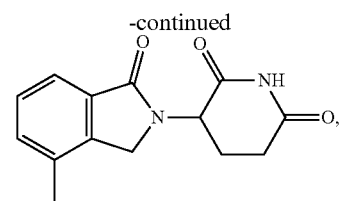

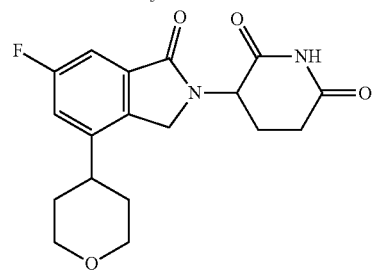

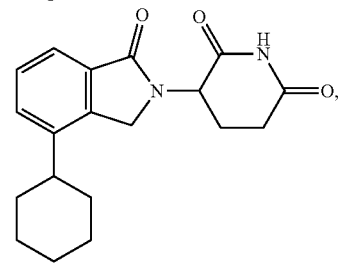

and pharmaceutically acceptable salt thereof.

Additional compounds disclosed herein include

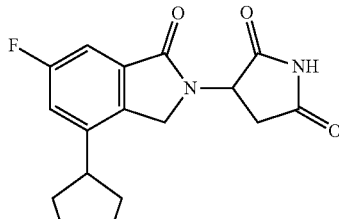

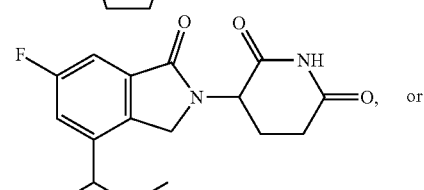

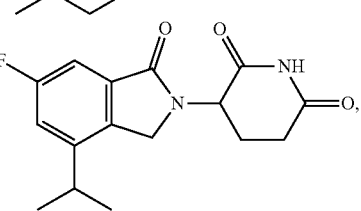

or a pharmaceutically acceptable salt thereof.

Pharmaceutical Compositions

Some embodiments provide a pharmaceutical composition comprising a compound described herein, including a compound of Formula (I), (Ia), (Ib) or (Ic), or a pharmaceutically acceptable salt thereof, and at least one pharmaceutically acceptable excipient or carrier.

The term "pharmaceutical composition" refers to a mixture of one or more compounds and/or salts disclosed herein with other chemical components, such as one or more excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, an "excipient" refers to essentially inert substances that are added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion or inhalation. For example, a buffered aqueous solution such as, without limitation, phosphate buffered saline that mimics the pH and isotonicity of human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound described herein, including a compound of Formula (I), (Ia), (Ib) or (Ic), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

The compounds, salt and/or pharmaceutical composition can be provided to an administering physician or other health care professional in the form of a kit. The kit is a package which houses a container which contains the compound(s) in a suitable pharmaceutical composition, and instructions for administering the pharmaceutical composition to a subject. The kit can optionally also contain one or more additional therapeutic agents. The kit can also contain separate doses of a compound(s) or pharmaceutical composition for serial or sequential administration. The kit can optionally contain one or more diagnostic tools and instructions for use. The kit can contain suitable delivery devices, for example, syringes, and the like, along with instructions for administering the compound(s) and any other therapeutic agent. The kit can optionally contain instructions for storage, reconstitution (if applicable), and administration of any or all therapeutic agents included. The kits can include a plurality of containers reflecting the number of administrations to be given to a subject.

Uses/Methods of Treatment

Some embodiments provide a method of treating or ameliorating cancer in a subject in need thereof, comprising administering an effective amount of a compound described herein, including a compound of Formula (I), (Ia), (Ib) or (Ic), or a pharmaceutically acceptable salt thereof, or a pharmaceutical composition thereof, to the subject. In some embodiments, the cancer is lymphoma, leukemia, multiple myeloma, skin cancer, brain cancer, lung cancer, retinal cell carcinoma, prostate cancer, ovarian cancer, liver cancer, adenocarcinoma, breast cancer, colorectal cancer, kidney cancer, bladder cancer, pancreatic cancer, or liposarcoma. In some embodiments, the cancer is mediated by the malfunction of one of more proteins, wherein the protein is a cytokine, PDE6, CK1α, or ikaros, or combinations thereof. In some such embodiments, the cytokine is TNFα, IL-1β, IL-2, or IL-6, or combinations thereof. In one embodiment, the disease is mediated by IL-2

In some embodiments, the lymphoma is Hodgkin's lymphoma, mantle cell lymphoma, or B-cell lymphoma. In some embodiments, the leukemia is acute lymphoblastic leukemia (ALL), acute myeloid leukemia (AML), chronic myeloid leukemia (CML), or chronic lymphocytic leukemia (CLL). In some embodiments, the skin cancer is melanoma or squamous cell carcinoma.

In some embodiments, the brain cancer is neuroblastoma, glioblastoma, or astrocytic glioma. In other embodiments, the lung cancer is non-small cell lung cancer or small cell lung cancer. In still other embodiments, the cancer is breast or ovarian cancer. In yet other embodiments, the cancer is retinal cell carcincoma, adenocarcinoma, or liposarcoma.

In some embodiments, the cancer is prostate cancer, liver cancer, colorectal cancer, kidney cancer, bladder cancer, or pancreatic cancer.

Some embodiments provide a method of ameliorating or treating a retinal disease in a subject in need thereof, comprising administering an effective amount of a compound described herein, including a compound of Formula (I), (Ia), (Ib) or (Ic), or a pharmaceutically acceptable salt thereof, or a pharmaceutical composition thereof, to the subject. In some embodiments, the retinal disease is retinitis pigmentosa (RP), autosomal dominant congenital stationary night blindness (adCSNB), achromatopsia (ACHM), and ciliopathy. In some embodiments, the ciliopathy is selected from retinal ciliopathy, Meckel-Gruber Syndrome, Joubert Syndrome (JBTS), Bardet-Biedl Syndrome, or Usher Syndrome. In some embodiments, the cancer is mediated by the malfunction of dysregulation of PDE6, for example, PDE6δ or PDE6D.

Some additional embodiments provide a method of ameliorating or treating an inflammatory disease, an autoimmune disease, an allergic disease, or a neurodegenerative disease in a subject in need thereof, comprising administering an effective amount of a compound described herein, including a compound of Formula (I), (Ia), (Ib) or (Ic), or a pharmaceutically acceptable salt thereof, or a pharmaceutical composition thereof, to the subject. In some embodiments, the inflammatory disease, autoimmune disease, allergic disease, or the neurodegenerative disease is fibrosis, multiple sclerosis, Alzheimer's disease, Parkinson's disease, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, chronic obstructive pulmonary disease, food allergies, asthma, or anaphylaxis. In some embodiments, the inflammatory disease, autoimmune disease, allergic disease, or the neurodegenerative disease is mediated by the malfunction, dysregulation, or inappropriate activation of one or more inflammatory cytokines, such as TNFα, IL-1β, or IL-6, or combinations thereof. In other embodiment, the inflammatory disease, autoimmune disease, allergic disease, or the neurodegenerative disease is caused by overexpression of dysregulation of IL-2.

In any embodiments of the treatment methods, the compound or salt thereof described herein may be co-administered with a second therapeutic agent.

Some embodiments provide a method of inhibiting the activity of CK1α in a cell, comprising contacting a cell with a compound described herein, including a compound of Formula (I), (Ia), (Ib) or (Ic), or a pharmaceutically acceptable salt thereof. In some embodiments, the cell possesses aberrant CK1α activity. Other embodiments provide a method of inhibiting the activity of PDE6 in a cell, comprising contacting a cell with a compound described herein, including a compound of Formula (I), (Ia), (Ib) or (Ic), or a pharmaceutically acceptable salt thereof. In some embodiments, the cell possesses aberrant PDE6 activity. In one embodiment, PDE6 is PDE6δ or PDE6D. Other embodiments provide a method of inhibiting the activity of ikaros in a cell, comprising contacting a cell with a compound described herein, including a compound of Formula (I), (Ia), (Ib) or (Tc), or a pharmaceutically acceptable salt thereof. In some embodiments, the cell possesses aberrant ikaros activity. In some embodiments, the CK1α is a CK1α mutant. In other embodiments, the CK1α is wild-type. In some embodiments, the PDE6 is a PDE6 mutant. In some embodiments, the PDE6 mutant is c. 140-1G>A PDE6D. In other embodiments, the PDE6 is wild-type. In some embodiments, the ikaros is a mutant. In other embodiments, the ikaros is wild-type. In some embodiments, the CK1α, PDE6, and/or ikaros is overexpressed.

Additional embodiments provide a method of modulating a cytokine in a cell, comprising contacting a cell with a compound described herein, including a compound of Formula (I), (Ia), (Ib) or (Ic), or a pharmaceutically acceptable salt thereof. In some embodiments, the cytokine is TNFα, IL-1β, IL-2, or IL-6, or combinations thereof. In some embodiments, the method inhibits one or more cytokine described herein. In one embodiment, the method downregulates IL-2.

In some embodiments, the cell is a cancer cell. In some embodiments, the cancer cell is selected from a Hodgkin's lymphoma cell, a mantle cell lymphoma cell, a B-cell lymphoma cell, an acute lymphoblastic leukemia (ALL) cell, an acute myeloid leukemia (AML) cell, a chronic myeloid leukemia (CML) cell, a chronic lymphocytic leukemia (CLL) cell, a multiple myeloma cell, a retinal cell carcinoma cell, a prostate cancer cell, an ovarian cancer cell, a squamous cell carcinoma cell, a melanoma cell, a liver cancer cell, a neuroblastoma cell, an adenocarcinoma cell, a non-small cell lung cancer cell, a small cell lung cancer cell, a breast cancer cell, a colorectal cancer cell, a brain cancer cell, a kidney cancer cell, a bladder cancer cell, a pancreatic cancer cell, a liposarcoma cell, a glioblastoma cell, an astrocytic glioma cell, a head and neck cancer cell, a thyroid cancer cell, and an osteosarcoma cell.

In some embodiments, the cell is in a subject in need of cancer treatment.

In some embodiments, the cell is a retinal cell in a subject in need of treatment for a retinal disease. In embodiments, the cell is in a subject in need of treatment for a retinal disease selected from: retinitis pigmentosa (RP), autosomal dominant congenital stationary night blindness (adCSNB), achromatopsia (ACHM), retinal ciliopathy, Meckel-Gruber Syndrome, Joubert Syndrome (JBTS), Bardet-Biedl Syndrome, and Usher Syndrome.

Various indicators for determining the effectiveness of a method for treating a cancer are known to those skilled in the art. Example of suitable indicators include, but are not limited to, a reduction in cell growth/proliferation, a reduction in tumor size, a reduction of morbidity or mortality in clinical outcomes, and/or other indicator of disease response.

In some embodiments, a compound described herein, including a compound of Formula (I), (Ia), (Ib) or (Ic), or a pharmaceutically acceptable salt thereof, can result in at least a 1, 2, 3, 4, 5, 10, 15, 20, 25, 50, 75, 100-fold or more reduction in the replication of cells and/or tumor size relative to pre-treatment levels in a subject, as determined several hours after receiving the initial dosage of the compound (for example, 60 hours after receiving the initial dosage of the compound). In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of cells and/or tumor size, as determined several hours after receiving the initial dosage of the compound (for example, 60 hours after receiving the initial dosage of the compound) compared to the reduction of replication of cells and/or tumor size achieved by the standard of care (for example, cytarabine, in combination with daunorubicin or idarubicin), or may achieve the same reduction as that of the standard of care in a shorter period of time, for example, in one day, two days, three days, four days or five days, as compared to the reduction achieved after 5 days of treatment with the standard of care.

After a period of time, cancer can develop resistance to one or more therapeutic agents. The term "resistance" as used herein refers to cancer cells displaying a delayed, lessened and/or null response to a therapeutic agent(s). For example, after treatment with an anticancer agent, the growth and/or spread of the cancer in a subject a resistant cancer may be reduced to a lesser degree compared to the growth and/or spread of the cancer in a subject with a non-resistant cancer. In some embodiments, a compound described herein, including a compound of Formula (I), (Ia), (Ib) or (Ic), or a pharmaceutically acceptable salt thereof, can be administered to a subject having cancer that is resistant to one or more different agents (for example, anticancer agents such as alkylating agents, plant alkaloids, antitumor antibiotics, antimetabolites, topoisomerase inhibitors, antimicrotubule agents, and checkpoint inhibitors). In some embodiments, development of resistant can be delayed when subjects are treated with a compound of Formula (I), or a pharmaceutically acceptable salt thereof, compared to the development cancer that is resistant to other drugs.

In some embodiments, a compound described herein, including a compound of Formula (I), (Ia), (Ib) or (Ic), or a pharmaceutically acceptable salt thereof, can decrease the percentage of subjects that experience complications from cancer compared to the percentage of subjects that experience complication being treated with the standard of care (for example, cytarabine in combination with daunorubicin or idarubicin). For example, the percentage of subjects being treated with a compound of Formula (I), or a pharmaceutically acceptable salt thereof, that experience complications can be 10%, 25%, 40%, 50%, 60%, 70%, 80% and 90% less compared to subjects being treated with cytarabine in combination with daunorubicin or idarubicin.

A potential advantage of utilizing a compound of Formula (I), (Ia), (Ib) or (Tc), or a pharmaceutically acceptable salt thereof, as described herein, may be creating a higher barrier to the development of resistance compared to the barrier when other compound(s) are administered. Additional advantages of utilizing a compound of Formula (I), (Ia), (Ib) or (Ic), or a pharmaceutically acceptable salt thereof, as described herein, may include lower toxicity; a reduction in side-effects; little to no significant effects on cytochrome P450; and/or little to no significant effects on p-glycoprotein; relative to other compounds, such as the standard of care (for example, cytarabine in combination with daunorubicin or idarubicin).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g., 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Additional Therapeutic Agents

Some embodiments provide pharmaceutical compositions comprising a compound described herein, including a compound of Formula (I), (Ia), (Ib) or (Ic), or a pharmaceutically acceptable salt of any of the foregoing and a second therapeutic agent. In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone. In some embodiments, the second therapeutic agent is mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; or oxaliplatin. In some embodiments, the second therapeutic agent is vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; or teniposide. In some embodiments, the second therapeutic agent is actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; or procarbazine. In some embodiments, the second therapeutic agent is cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; or floxuridine. In some embodiments, the second therapeutic agent is azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; or triethylenemelamine. In some embodiments, the second therapeutic agent is nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; or eribulin. In some embodiments, the second therapeutic agent is azathioprine; mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; or ocrelizumab. In some embodiments, the second therapeutic agent is pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pembrolizumab; pexelizumab; reslizumab; rovelizumab; siplizumab; talizumab; telimomab; vapaliximab; vepalimomab; abatacept; belatacept; pegsunercept; aflibercept; alefacept; or rilonacept.

EXAMPLES

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

Characterization of the compounds disclosed herein was performed with Bruker AV-500 and DRX-500 NMR spectrometers and a Perkin Elmer PE-SCIEX API-150 mass spectrometer.

Example 1. Compound 1: 3-(4-Cyclopentyl-6-fluoro-2-isoindolinoyl)-2,6-piperidinedione

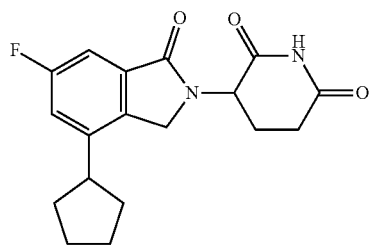 [SMILES: O=C1CCC(N2Cc3c(cc(F)cc3C3CCCC3)C2=O)C(=O)N1]

To a solution of methyl 3-bromo-5-fluoro-2-methylbenzoate (1.92 g, 7.79 mmol) in $CCl_4$ (45 mL) was added NBS (1.43 g, 8.03 mmol). Dibenzoylperoxide (250 mg, 0.76 mmol) was added and the mixture was heated at 80° C. for 4 h. The mixture was cooled to RT, diluted with DCM, and washed with saturated aq. NaHCO₃. The organic layer was dried over MgSO₄, filtered, and concentrated to give methyl 3-bromo-2-(bromomethyl)-5-fluorobenzoate (2.54 g, quant yield) as an oil.

Methyl 3-bromo-2-(bromomethyl)-5-fluorobenzoate (2.54 g, 7.79 mmol) was dissolved in ACN (15 ml) and added to a mixture of tert-butyl 4,5-diamino-5-oxopentanoate hydrochloride (1.85 g, 7.79 mmol) and K₂CO₃ (2.70 g, 19.5 mmol) in ACN (45 mL). The mixture was heated at 60° C. for 2 h, concentrated, dissolved in EA, and washed with H₂O. The organic layer was dried over MgSO₄, filtered, and concentrated to give tert-butyl 5-amino-4-(4-bromo-6-fluoro-1-oxoisoindolin-2-yl)-5-oxopentanoate (2.87 g, 89% yield) as a solid.

To a solution of tert-butyl 5-amino-4-(4-bromo-6-fluoro-1-oxoisoindolin-2-yl)-5-oxopentanoate (1.50 g, 3.61 mmol) in toluene/H₂O (23 mL:3 mL) was added 2-(cyclopent-1-en-1-yl)-4,4,5,5-tetramethyl-1,3,2-dioxaborolane (840 mg, 4.33 mmol), followed by K₂CO₃ (1.28 g, 9.26 mmol) and Pd(dppf)Cl₂ (600 mg, 0.735 mmol). After purging with N₂, the mixture was heated at 85° C. for 16 h. The mixture was cooled to RT, filtered through CELITE®, diluted with EA, and washed with H₂O. The organic layer was dried over MgSO₄, filtered, and concentrated. The residue was purified using silica gel (Biotage) eluting with EA to give tert-butyl 5-amino-4-(4-(cyclopent-1-en-1-yl)-6-fluoro-1-oxoisoindolin-2-yl)-5-oxopentanoate (938 mgs, 65% yield).

To a solution of tert-butyl 5-amino-4-(4-(cyclopent-1-en-1-yl)-6-fluoro-1-oxoisoindolin-2-yl)-5-oxopentanoate (1.04 g, 2.59 mmol) in MeOH (40 mL) was added Pd/C (catalytic). The mixture was stirred for 16 h under H₂ then filtered through CELITE® and concentrated to give tert-butyl 5-amino-4-(4-cyclopentyl-6-fluoro-1-oxoisoindolin-2-yl)-5-oxopentanoate (805 mg, 77% yield).

To a solution of tert-butyl 5-amino-4-(4-cyclopentyl-6-fluoro-1-oxoisoindolin-2-yl)-5-oxopentanoate (805 mg, 1.99 mmol) in DCM (30 mL) was added TFA (10 mL). The mixture was stirred for 3 h then concentrated. ACN (40 mL) was added followed by CDI (1.30 g, 8.07 mmol) and TEA (0.5 mL). The mixture was heated at 80° C. for 2 h then concentrated, dissolved in EA, and washed with saturated NaHCO₃. The organic layer was dried over MgSO₄, filtered, and concentrated. The residue was purified using silica gel (Biotage) eluting with EA to give 3-(4-cyclopentyl-6-fluoro-1-oxoisoindolin-2-yl)piperidine-2,6-dione (320 mg, 50% yield) as a solid. MS (ESI) m/z 331.3 [M+H]⁺. ¹H NMR (400 MHz, DMSO-d₆) δ 10.99 (s, 1H), 7.34 (m, 1H), 7.32 (m, 1H), 5.12 (d, 1H), 4.34-4.47 (m, 2H), 3.07-2.88 (m, 2H), 2.62 (d, 1H), 2.44 (m, 1H), 1.98-2.04 (m, 3H), 1.80 (m, 2H), 1.59-1.65 (m, 4H).

Example 2. Compound 2: 3-(4-Cyclopentyl-2-isoindolinoyl)-2,6-piperidinedione

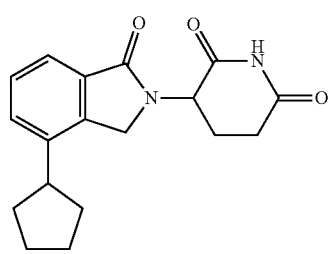 [SMILES: O=C1CCC(N2Cc3c(cccc3C3CCCC3)C2=O)C(=O)N1]

Compound 2 was prepared analogously to Compound 1 but using tert-butyl 5-amino-4-(4-bromo-1-oxoisoindolin-2-yl)-5-oxopentanoate instead of tert-butyl 5-amino-4-(4-bromo-6-fluoro-1-oxoisoindolin-2-yl)-5-oxopentanoate. MS (ESI) m/z 313.1 [M+H]⁺.

Example 3. Compound 3: 3-(4-Cyclohexyl-6-fluoro-2-isoindolinoyl)-2,6-piperidinedione

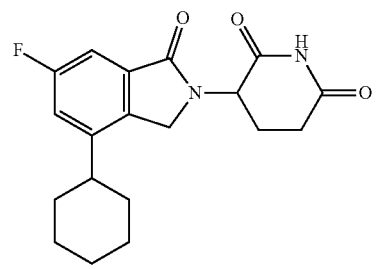 [SMILES: O=C1CCC(N2Cc3c(cc(F)cc3C3CCCCC3)C2=O)C(=O)N1]

Compound 3 was prepared analogously to Compound 1, but using 2-(cyclohex-1-en-1-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 345.1 [M+H]⁺.

Example 4. Compound 4: 3-(4-cyclopentyl-6-fluoro-1-oxoisoindolin-2-yl)-3-methylpiperidine-2,6-dione

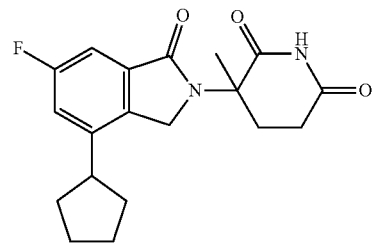 [SMILES: CC1(N2Cc3c(cc(F)cc3C3CCCC3)C2=O)CCC(=O)NC1=O]

To a solution of 3-amino-3-methylpiperidine-2,6-dione (520 mg, 2.91 mmol, HCl salt) in DMF (12 mL) at 0° C. was added TEA (736.6 mg, 7.279 mmol) and methyl 3-bromo-2-(bromomethyl)-5-fluorobenzoate (788.5 mg, 2.426 mmol). The mixture was heated at 50° C. overnight. The mixture was concentrated and the residue was purified using silica gel eluting with MeOH in DCM from 0% to 5% to give 3-(4-bromo-6-fluoro-1-oxoisoindolin-2-yl)-3-methylpiperidine-2,6-dione (552 mg, 64% yield) as a solid.

To a solution of 3-(4-bromo-6-fluoro-1-oxoisoindolin-2-yl)-3-methylpiperidine-2,6-dione (250 mg, 0.7062 mmol) in DMF (15 mL) was added 2-(cyclopent-1-en-1-yl)-4,4,5,5-tetramethyl-1,3,2-dioxaborolane (205.5 mg, 1.059 mmol) and K₂CO₃ (194.9 mg, 1.412 mmol). The mixture was purged with N₂ and Pd(dppf)Cl₂ (206.7 mg, 0.2825 mmol) was added. The mixture was heated at 100° C. overnight then concentrated. The resulting residue was diluted with H₂O and extracted with DCM. The combined organic layers were dried over Na₂SO₄, filtered, and concentrated. The residue was purified using silica gel eluting with EA in PE from 10% to 80% to give 3-(4-(cyclopent-1-en-1-yl)-6- fluoro-1-oxoisoindolin-2-yl)-3-methylpiperidine-2,6-dione (150 mg, 62% yield) as a solid.

To a solution of 3-(4-(cyclopent-1-en-1-yl)-6-fluoro-1-oxoisoindolin-2-yl)-3-methylpiperidine-2,6-dione (150 mg, 0.439 mmol) in MeOH (4 mL) and DCM (3 mL) was added Pd/C (200 mg). The mixture was purged with H₂ then stirred under H₂ for 12 h. The mixture was filtered and the filtrate was concentrated. The residue was purified using silica gel eluting with EA in petroleum from 1% to 90% to afford Compound 4 (84.6 mg, 56% yield) as a solid. ¹H NMR (400 MHz, DMSO-d₆) δ 10.90 (s, 1H), 7.37-7.40 (m, 1H), 7.21-7.24 (m, 1H), 4.64-4.75 (m, 2H), 3.08-3.12 (m, 1H), 2.71-2.76 (m, 1H), 2.60-2.68 (m, 1H), 2.54-2.55 (m, 1H), 2.05-2.07 (m, 2H), 1.86-1.91 (m, 1H), 1.82 (s, 2H), 1.70 (s, 3H), 1.60-1.67 (m, 4H). MS (ESI) m/z 345 [M+H]⁺.

Example 5. Compound 5: 3-(4-Cyclopropyl-6-fluoro-2-isoindolinoyl)-2,6-piperidinedione

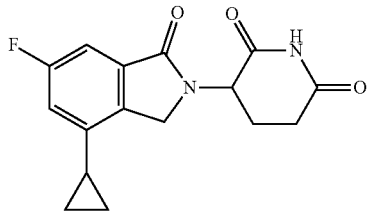 [SMILES: O=C1CCC(N2Cc3c(cc(F)cc3C3CC3)C2=O)C(=O)N1]

Compound 5 was prepared analogously to Compound 1 but using 2-cyclopropyl-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 303.0 [M+H]⁺. ¹H NMR (400 MHz, DMSO-d₆) δ 11.00 (s, 1H), 7.29-7.27 (m, 1H), 7.03-7.00 (m, 1H), 5.14 (dd, J=4.8, 13.2 Hz, 1H), 4.55-4.35 (m, 2H), 2.97-2.88 (m, 1H), 2.63-2.59 (m, 1H), 2.47-2.40 (m, 1H), 2.05-2.02 (m, 1H), 1.97-1.91 (m, 1H), 1.03-1.01 (m, 2H), 0.85-0.84 (m, 2H).

Example 6. Compound 6: 3-(4-cyclopentyl-6-fluoro-1-oxoisoindolin-2-yl)-4-methylpiperidine-2,6-dione

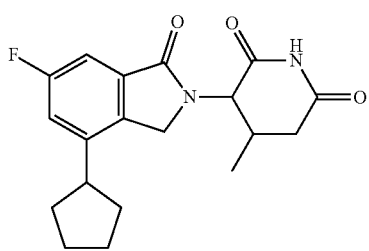 [SMILES: CC1CC(=O)NC(=O)C1N1Cc2c(cc(F)cc2C2CCCC2)C1=O]

To a solution of 3-amino-4-methylpiperidin-2-one (76 mg, 0.59 mmol) in DMF (4 mL) at 0° C. was added N,N-diisopropylethylamine (159 mg, 1.24 mmol) and 3-bromo-2-(bromomethyl)-5-fluorobenzoate (160 mg, 0.494 mmol). The mixture was heated at 50° C. overnight. The mixture was concentrated and the residue was purified using silica gel eluting with MeOH in DCM from 0% to 5% to give 4-bromo-6-fluoro-2-(4-methyl-2-oxopiperidin-3-yl)isoindolin-1-one (152 mg, 91% yield) as a solid.

To a solution of 4-bromo-6-fluoro-2-(4-methyl-2-oxopiperidin-3-yl)isoindolin-1-one (152 mg, 0.4470 mmol) in toluene/water (10 mL/1 mL) was added 2-(cyclopent-1-en-1-yl)-4,4,5,5-tetramethyl-1,3,2-dioxaborolane (130 mg, 0.671 mmol) and K₂CO₃ (123.4 mg, 0.894 mmol). The mixture was purged with N₂ and Pd(dppf)Cl₂ (131 mg, 0.179 mmol) was added. The mixture was heated at 100° C. overnight then concentrated. The residue was diluted with H₂O and extracted with DCM. The combined organic layers were dried over Na₂SO₄, filtered, and concentrated. The residue was purified using silica gel eluting with EA in PE from 10% to 100% to give 4-(cyclopent-1-en-1-yl)-6-fluoro-2-(4-methyl-2-oxopiperidin-3-yl)isoindolin-1-one (75 mg, 52% yield) as a solid.

To a solution of 4-(cyclopent-1-en-1-yl)-6-fluoro-2-(4-methyl-2-oxopiperidin-3-yl)isoindolin-1-one (75 mg, 0.2286 mmol) in MeOH (3 mL) and DCM (1.5 mL) was added Pd/C (100 mg). The mixture was purged with H₂ then stirred under H₂ for 12 h. The mixture was filtered and concentrated. The residue was purified using silica gel eluting with EA in petroleum from 1% to 90% to give 4-cyclopentyl-6-fluoro-2-(4-methyl-2-oxopiperidin-3-yl)isoindolin-1-one (75.4 mg, 99.5% yield) as a solid.

To a solution of 4-cyclopentyl-6-fluoro-2-(4-methyl-2-oxopiperidin-3-yl)isoindolin-1-one (65.4 mg, 0.198 mmol) in ACN (12 mL) was added Dess-Martin (185 mg, 0.436 mmol) and wet DMSO (18 drops). The mixture was heated at 120° C. for 45 min under microwave. The mixture was cooled to RT and quenched with saturated Na₂S₂O₃ (5 mL). The mixture was extracted with DCM. The combined organic layers were washed with NaHCO₃ (sat.)/Na₂S₂O₃ (10%) (1:1), dried over Na₂SO₄, filtered, and concentrated. The residue was purified using silica gel eluting with EA in petroleum from 10% to 60% to give Compound 6 (27.9 mg, 36% yield) as a solid. ¹H NMR (400 MHz, DMSO-d₆) δ 11.04 (s, 1H), 7.37-7.40 (m, 1H), 7.32-7.35 (m, 1H), 4.89 (d, J=11.6 Hz, 1H), 4.24-4.45 (m, 2H), 3.06-3.10 (m, 1H), 2.60-2.69 (m, 3H), 2.05 (s, 2H), 1.80 (s, 2H), 1.63 (s, 4H), 0.90 (d, J=5.6 Hz, 3H). MS (ESI) m/z 345 [M+H]⁺.

Example 7. Compound 7: 3-[4-(4,4-Dimethylcyclohexyl)-6-fluoro-2-isoindolinoyl]-2,6-piperidinedione

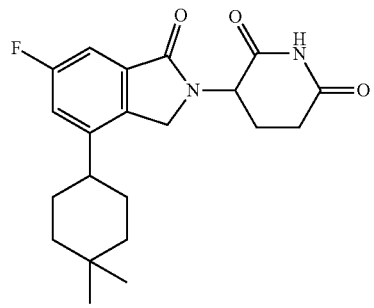 [SMILES: CC1(C)CCC(c2cc(F)cc3c2CN(C2CCC(=O)NC2=O)C3=O)CC1]

Compound 7 was prepared analogously to Compound 1 but using tert-butyl 5-amino-4-(4-(4,4-dimethylcyclohex-1-en-1-yl)-6-fluoro-1-oxoisoindolin-2-yl)-5-oxopentanoate instead of tert-butyl 5-amino-4-(4-(cyclopent-1-en-1-yl)-6-fluoro-1-oxoisoindolin-2-yl)-5-oxopentanoate. MS (ESI) m/z 372.43 [M+H]⁺. ¹H NMR (400 MHz, DMSO-d₆) δ 10.999 (s, 1H), 7.47-7.44 (d, 1H), 7.34-7.32 (d, 1H), 5.13-5.122 (dd, 1H), 4.468 (d, 1H), 4.33 (d, 1H), 2.954-2.881 (t, 1H), 2.61-2.49 (m, 2H), 2.44-2.41 (d, 1H), 2.025-1.99 (m, 1H), 1.699-1.60 (m, 4H), 1.47 (d, 2H), 1.34-1.299 (t, 2H), 1.005 (s, 3H), 0.941 (s, 3H).

Example 8. Compound 8: 3-[4-(4,4-Dimethyl-1-cyclohexen-1-yl)-6-fluoro-2-isoindolinoyl]-2,6-piperidinedione

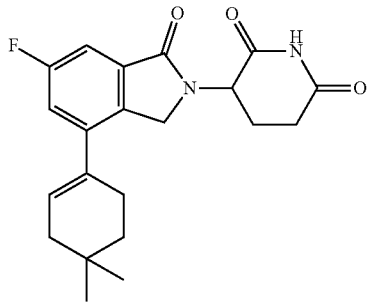 [SMILES: CC1(C)CC=C(c2cc(F)cc3c2CN(C2CCC(=O)NC2=O)C3=O)CC1]

Compound 8 was prepared analogously to Compound 1 but using 2-(4,4-dimethyl-1-cyclohexen-1-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 371.1 [M+H]$^+$.

Example 9. Compound 9: 3-[4-(4,4-Difluoro-1-cyclohexen-1-yl)-6-fluoro-2-isoindolinoyl]-2,6-piperidinedione

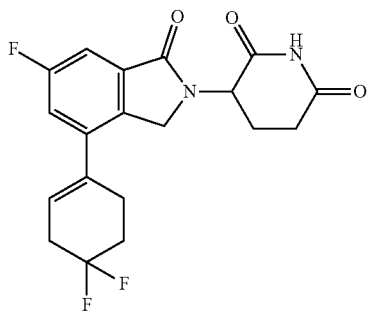 [SMILES: O=C1CCC(N2Cc3c(cc(F)cc3C3=CCC(F)(F)CC3)C2=O)C(=O)N1]

Compound 9 was prepared analogously to Compound 1 but using 2-(4,4-difluoro-1-cyclohexen-1-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 379.1 [M+H]$^+$.

Example 10. Compound 10: 4-cyclopentyl-2-(2,6-dioxopiperidin-3-yl)isoindoline-1,3-dione

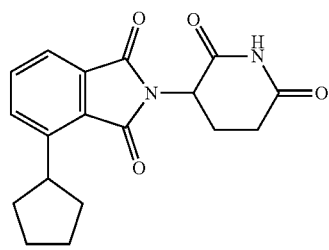 [SMILES: O=C1CCC(N2C(=O)c3cccc(C4CCCC4)c3C2=O)C(=O)N1]

To a solution of 3-bromophthalic acid (3.20 g, 12.3 mmol) in DMF (16 mL) was added NaHCO$_3$ (1.2 g, 14.7 mmol), followed by iodomethane (0.92 mL, 14.7 mmol). The mixture was heated at 75° C. for 3 h. The mixture was cooled to RT then diluted with H$_2$O and extracted with tert-butyl methyl ether. The combined organic layers were washed with brine (60 mL), dried over Na$_2$SO$_4$, filtered, and concentrated. The residue was purified using silica gel eluting with PE/EA from 50:1 to 10:1 to give dimethyl 3-bromophthalate (3.7 g, 84% yield) as a solid.

To a mixture of dimethyl 3-bromophthalate (1.00 g, 3.67 mmol) in dioxane/H$_2$O (20 mL/2 mL) was added 2-(cyclopent-1-en-1-yl)-4,4,5,5-tetramethyl-1,3,2-dioxaborolane (852 mg, 4.40 mmol) and K$_2$CO$_3$ (1.26 g, 9.15 mmol). The mixture was purged with N$_2$ then Pd(dppf)Cl$_2$ (536 mg, 0.73 mmol) was added. The mixture was heated at 100° C. overnight then concentrated. The residue was diluted with H$_2$O and extracted with EA. The combined organic layers were dried over Na$_2$SO$_4$, filtered, and concentrated. The residue was purified by prep-TLC eluting with EA to give dimethyl 3-(cyclopent-1-en-1-yl)phthalate (876 mg, 92% yield) as an oil.

To a solution of dimethyl 3-(cyclopent-1-en-1-yl)phthalate (876 mg, 3.37 mmol) in MeOH (15 mL) was added 10% Pd/C (180 mg). The mixture was purged with H$_2$ then stirred overnight under H$_2$. The mixture was filtered and concentrated to give dimethyl 3-cyclopentylphthalate (951 mg, crude).

To a solution of dimethyl 3-cyclopentylphthalate (951 mg, 3.63 mmol) in dioxane (6 mL) was added 2N NaOH (3.63 mL, 7.26 mmol). The mixture was heated at 85° C. for 48 h then concentrated. The residue was adjusted to a pH of 3 using 2N HCl then extracted with EA. The organic phase was dried over Na$_2$SO$_4$, filtered, and concentrated to give crude 3-cyclopentylphthalic acid (800 mg) as a solid.

The solution of 3-cyclopentylphthalic acid (100 mg, 0.43 mmol) in acetic anhydride (5 mL) was heated at 140° C. for 3 h then concentrated to give 4-cyclopentylisobenzofuran-1,3-dione (100 mg, crude) as a solid.

To a solution of 4-cyclopentylisobenzofuran-1,3-dione (100 mg, 0.46 mmol) in acetic acid (5 mL) was added 3-aminopiperidine-2,6-dione (76 mg, 0.46 mmol) and sodium acetate (75 mg, 0.92 mmol). The mixture was heated at 130° C. overnight then concentrated. The residue was purified by prep-TLC eluting with EA to give Compound 10 (54 mg, 36% yield) as a solid. MS (ESI) m/z 327.1 [M+H]$^+$. $^1$HNMR (DMSO-d$_6$, 400 MHz) δ 11.11 (s, 1H), 7.83-7.79 (m, 2H), 7.74-7.72 (m, 1H), 5.12 (dd, J=5.2, 12.8 Hz, 1H), 4.04-4.00 (m, 1H), 2.90-2.85 (m, 1H), 2.61-2.55 (m, 1H), 2.50-2.49 (m, 1H), 2.48-2.46 (m, 1H), 2.07-2.06 (m, 2H), 2.05-2.03 (m, 2H), 1.70-1.61 (m, 4H).

Example 11. Compound 11: 3-[4-(4,4-Difluorocyclohexyl)-6-fluoro-2-isoindolinoyl]-2,6-piperidinedione

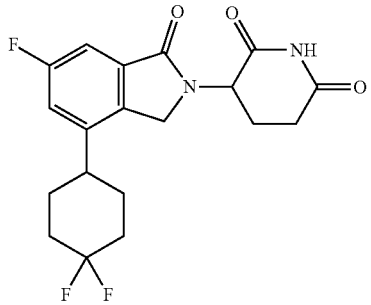 [SMILES: O=C1CCC(N2Cc3c(cc(F)cc3C3CCC(F)(F)CC3)C2=O)C(=O)N1]

Compound 11 was prepared analogously to Compound 1 but using tert-butyl 5-amino-4-(4-(4,4-difluorocyclohex-1-en-1-yl)-6-fluoro-1-oxoisoindolin-2-yl)-5-oxopentanoate instead of tert-butyl 5-amino-4-(4-(cyclopent-1-en-1-yl)-6-fluoro-1-oxoisoindolin-2-yl)-5-oxopentanoate. MS (ESI) m/z 380.36 [M+H]$^+$. $^1$H NMR (400 MHz, DMSO-d$_6$) δ 11.024 (s, 1H), 7.381 (d, 1H), 7.36 (d, 1H), 5.16-5.14 (d, 1H), 4.504 (d, 1H), 4.376 (d, 1H), 2.996-2.931 (m, 1H), 2.904-2.81 (t, 1H), 2.63-2.60 (d, 1H), 2.49-2.37 (m, 1H), 2.043-2.017 (m, 4H), 1.47 (t, 2H), 1.914-1.86 (m, 2H), 1.80-1.73 (m, 3H), 1.70-1.68 (m, 2H).

Example 12. Compound 12: 3-(4-Cyclopentyl-6-fluoro-3-oxo-2-isoindolinoyl)-2,6-piperidinedione

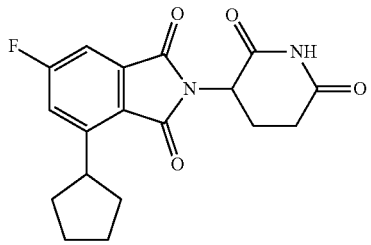 [SMILES: O=C1CCC(N2C(=O)c3cc(F)cc(C4CCCC4)c3C2=O)C(=O)N1]

Compound 12 was prepared analogously to Compound 10 but using 3-bromo-5-fluorophthalic acid instead of 3-bromophthalic acid. MS (ESI) m/z 345.1 [M+H]$^+$. $^1$H NMR (400 MHz, DMSO-d$_6$) δ 11.12 (s, 1H), 7.68-7.62 (m, 2H), 5.13 (dd, J=5.6, 12.8 Hz, 1H), 4.01-3.97 (m, 1H), 2.93-2.84 (m, 1H), 2.62-2.46 (m, 2H), 2.08-2.02 (m, 3H), 1.82-1.79 (m, 2H), 1.71-1.59 (m, 4H).

Example 13. Compound 13: 3-(4-Cyclopropyl-2-isoindolinoyl)-2,6-piperidinedione

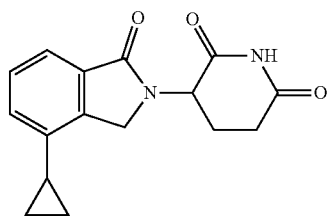 [SMILES: O=C1CCC(N2Cc3c(cccc3C3CC3)C2=O)C(=O)N1]

Compound 13 was prepared analogously to Compound 5 but using tert-butyl 5-amino-4-(4-bromo-1-oxoisoindolin-2-yl)-5-oxopentanoate instead of tert-butyl 5-amino-4-(4-bromo-6-fluoro-1-oxoisoindolin-2-yl)-5-oxopentanoate. MS (ESI) m/z 285.1 [M+H]$^+$. $^1$H NMR (400 MHz, DMSO-d$_6$) δ 11.00 (s, 1H), 7.52 (d, J=7.2 Hz, 1H), 7.42 (t, J=7.6 Hz, 1H), 7.16 (d, J=7.2 Hz, 1H), 5.14 (dd, J=4.8, 13.2 Hz, 1H), 4.57-4.36 (m, 2H), 2.93-2.90 (m, 1H), 2.63-2.58 (m, 1H), 2.46-2.41 (m, 1H), 2.04-2.01 (m, 1H), 1.94-1.91 (m, 1H), 1.00-0.98 (m, 2H), 0.80-0.75 (m, 2H).

Example 14. Compound 14: 3-(4-Cyclopentyl-6-methoxy-2-isoindolinoyl)-2,6-piperidinedione

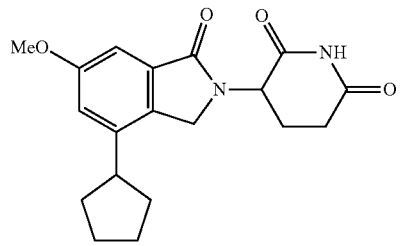 [SMILES: COc1cc2c(c(C3CCCC3)c1)CN(C1CCC(=O)NC1=O)C2=O]

Compound 14 was prepared analogously to Compound 1 but using 6-bromo-4-methoxy-2-toluate instead of 3-bromo-5-fluoro-2-methylbenzoate. MS (ESI) m/z 343.1 [M+H]$^+$. $^1$H NMR (400 MHz, DMSO-d$_6$) δ 10.97 (s, 1H), 7.07-7.04 (m, 2H), 5.11 (dd, J=4.8, 13.2 Hz, 1H), 4.43-4.23 (m, 2H), 3.82 (s, 3H), 3.05-2.87 (m, 2H), 2.61-2.57 (m, 1H), 2.46-2.39 (m, 1H), 2.02-1.99 (m, 3H), 1.80-1.77 (m, 2H), 1.66-1.56 (m, 4H).

Example 15. Compound 15: 3-(4-Cycloheptyl-6-fluoro-2-isoindolinoyl)-2,6-piperidinedione

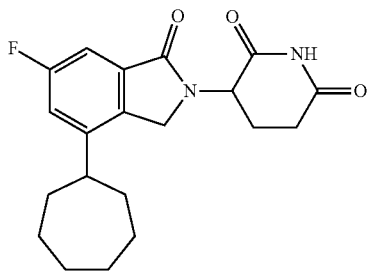 [SMILES: O=C1CCC(N2Cc3c(cc(F)cc3C3CCCCCC3)C2=O)C(=O)N1]

Compound 15 was prepared analogously to Compound 1 but using 2-(1-cyclohepten-1-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 358.41 [M+H]$^+$. $^1$H NMR (400 MHz, DMSO-d$_6$) δ 11.01 (s, 1H), 7.36-7.39 (m, 2H), 5.15-5.11 (dd, 1H), 4.491 (d, 1H), 4.33 (d, 1H), 2.954-2.881 (t, 1H), 2.891-2.88 (t, 1H), 2.79-2.75 (d, 1H), 2.5-2.49 (d, 1H), 2.039-2.01 (m, 1H), 1.80-1.78 (bm, 4H), 1.70-1.68 (m, 4H), 1.005 (s, 3H), 1.6-1.5 (m, 4H).

Example 16. Compound 16: 3-(4-Cyclopentyl-5,6-difluoro-2-isoindolinoyl)-2,6-piperidinedione

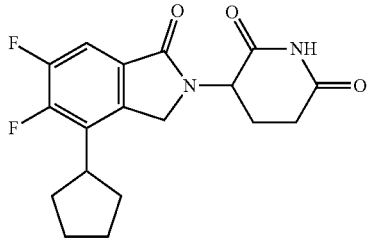

Compound 16 was prepared analogously to Compound 1 but using tert-butyl 5-amino-4-(4-bromo-5,6-difluoro-1-oxoisoindolin-2-yl)-5-oxopentanoate instead of tert-butyl 5-amino-4-(4-bromo-6-fluoro-1-oxoisoindolin-2-yl)-5-oxopentanoate. MS (ESI) m/z 348.8 [M+H]$^+$. $^1$H NMR (400 MHz, DMSO-d$_6$) δ 11.01 (s, 1H), 7.62 (t, 1H), 5.10-5.13 (m, 1H), 4.50-4.53 (d, 1H), 4.38-4.40 (d, 1H), 3.12-3.17 (m, 1H), 2.94-2.99 (m, 1H), 2.51-2.55 (m, 1H), 2.43-2.48 (m, 1H), 1.99-2.05 (m, 3H), 1.83-1.90 (m, 2H), 1.66-1.80 (m, 4H).

Example 17. Compound 17: 3-(4-(Difluoromethyl)-6-fluoro-1-oxoisoindolin-2-yl) piperidine-2,6-dione

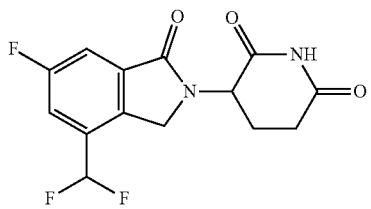 [SMILES: O=C1CCC(N2Cc3c(cc(F)cc3C(F)F)C2=O)C(=O)N1]

A mixture of methyl 3-bromo-5-fluoro-2-methylbenzoate (3.00 g, 12.2 mmol), Zn(CN)$_2$ (1.12 g, 9.7 mmol) and Pd(PPh$_3$)$_4$ (1.4 g, 0.09 mmol) in DMF (20 mL) was stirred at 100° C. under N$_2$ for 6 h. The mixture was concentrated and poured into H$_2$O then extracted with tert-butyl methyl ether. The combined organic layers were dried over Na$_2$SO$_4$, filtered, and concentrated. The residue was purified using silica gel eluting with PE/EA from 50:1 to 20:1 to give methyl 3-cyano-5-fluoro-2-methylbenzoate (2.73 g, 87% yield) as a solid.

To a solution of methyl 3-cyano-5-fluoro-2-methylbenzoate (600 mg, 3.10 mmol) in pyridine/H$_2$O/acetic acid (5 mL/5 mL/5 mL) at 0° C. was added NaH$_2$PO$_2$ (2.14 g, 24.8 mmol) and Raney Ni (1.0 g). After 5 h at 0° C., the mixture was acidified using 1N HCl and extracted with DCM. The organic phase was washed with brine, dried over Na$_2$SO$_4$, filtered, and concentrated. The residue was purified using silica gel eluting with EA in PE from 0% to 5% to give methyl 5-fluoro-3-formyl-2-methylbenzoate (200 mg, 33% yield) as an oil.

To a solution of methyl 5-fluoro-3-formyl-2-methylbenzoate (300 mg, 1.5 mmol) in DCM (20 mL) was added DAST (1.11 g, 7.6 mmol). The mixture was stirred overnight then cooled to 0° C., neutralized using saturated NaHCO$_3$ (aq.), and extracted with DCM. The combined organic layers were dried over Na$_2$SO$_4$, filtered, and concentrated. The residue was purified using silica gel eluting with EA in PE from 0% to 10% to give methyl 3-(difluoromethyl)-5-fluoro-2-methylbenzoate (208 mg, 46% yield) as a solid.

To a solution of methyl 3-(difluoromethyl)-5-fluoro-2-methylbenzoate (200 mg, 0.70 mmol) in carbon tetrachloride (6 mL) was added NBS (138 mg, 0.77 mmol) and benzoyl peroxide (17 mg, 0.07 mmol). The mixture was heated at 80° C. overnight then filtered and concentrated. The residue was purified using silica gel eluting with EA in PE from 0% to 10% to give methyl 2-(bromomethyl)-3-(difluoromethyl)-5-fluorobenzoate (240 mg, 53% yield) as an oil.

To a solution of methyl 2-(bromomethyl)-3-(difluoromethyl)-5-fluorobenzoate (140 mg, 60% purity, 0.284 mmol) in DMF (5 mL) was added 3-aminopiperidine-2,6-dione (46.7 mg, 0.284 mmol) and TEA (86.0 mg, 0.85 mmol). The mixture was heated at 50° C. for 2 h then diluted with H$_2$O and extracted with EA. The combined organic layers were concentrated then the residue was triturated with DCM to give Compound 17 (41.8 mg, 28% yield) as a solid. MS (ESI) m/z 313.0 [M+H]$^+$. $^1$H NMR (DMSO-d$_6$, 400 MHz) δ: 11.02 (s, 1H), 7.76-7.72 (m, 2H), 7.26 (t, J=54.8 Hz, 1H), 5.16 (dd, J=13.2, 4.8 Hz, 1H), 4.60 (d, J=17.6 Hz, 1H), 4.60 (d, J=18.0 Hz, 1H), 2.96-2.86 (m, 1H), 2.62-2.57 (m, 1H), 2.50-2.43 (m, 1H), 2.06-2.01 (m, 1H).

Example 18. Compound 18: 3-(4-Cyclopentyl-6-fluoro-1-oxoisoindolin-2-yl)-3-ethylpiperidine-2,6-dione

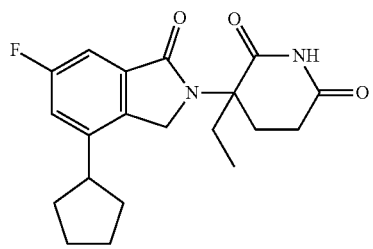 [SMILES: CCC1(N2Cc3c(cc(F)cc3C3CCCC3)C2=O)CCC(=O)NC1=O]

To a solution of 5-fluoro-2-methylbenzoic acid (3.00 g, 19.5 mmol) in H$_2$SO$_4$ (30 mL) at 0° C. was added NBS (3.40 g, 19.5 mmol). After 3 h at 0° C., the mixture was warmed to RT and stirred overnight. The mixture was poured slowly into ice water and extracted with EA. The organic phase was washed with brine, dried over Na$_2$SO$_4$, filtered, and concentrated to give 3-bromo-5-fluoro-2-methylbenzoic acid (4.2 g, crude) as a solid.

To a solution of 3-bromo-5-fluoro-2-methylbenzoic acid (4.2 g, crude) in MeOH (16 mL) was added thionyl chloride (2.5 mL) dropwise. The mixture was heated at 90° C. for 3 h then concentrated. The residue was purified using silica gel eluting with EA in PE from 0% to 3% to give the methyl 3-bromo-5-fluoro-2-methylbenzoate (2.3 g, 51% yield) as an oil.

To a solution of methyl 3-bromo-5-fluoro-2-methylbenzoate (2.00 g, 8.13 mmol) in carbon tetrachloride (20 mL) was added NBS (2.20 g, 12.2 mmol) and AIBN (533 mg, 3.25 mmol). The mixture was heated at 90° C. overnight then concentrated. The residue was purified using silica gel eluting with EA in PE from 0% to 3% to give the methyl 3-bromo-2-(bromomethyl)-5-fluorobenzoate (2.5 g, 96% yield) as an oil.

To a solution of methyl 3-bromo-2-(bromomethyl)-5-fluorobenzoate (1.19 g, 3.67 mmol) and TEA (927 mg, 9.18 mmol) in DMF (20 mL) was added the solution of 3-amino-3-ethylpiperidine-2,6-dione (837 mg, 4.4 mmol) in DMF (2 mL). The mixture was heated at 50° C. for 3 h then concentrated. The residue was triturated with EA to give 3-(4-bromo-6-fluoro-1-oxoisoindolin-2-yl)-3-ethylpiperidine-2,6-dione (870 mg, 64% yield) as a solid.

To a solution of 3-(4-bromo-6-fluoro-1-oxoisoindolin-2-yl)-3-ethylpiperidine-2,6-dione (770 mg, 2.09 mmol) in dioxane/H$_2$O (15 mL/15 mL) was added 2-(cyclopent-1-en-1-yl)-4,4,5,5-tetramethyl-1,3,2-dioxaborolane (487 mg, 2.51 mmol) and K$_2$CO$_3$ (722 mg, 5.23 mmol). The mixture was purged with N$_2$ then Pd(dppf)Cl$_2$ (307 g, 0.42 mmol) was added. The mixture was heated at 100° C. for 3 h then cooled to RT and filtered. The filtrate was concentrated and the residue was purified using silica gel eluting with EA in PE from 0% to 9% to give 3-(4-(cyclopent-1-en-1-yl)-6-fluoro-1-oxoisoindolin-2-yl)-3-ethylpiperidine-2,6-dione (509 mg, 68% yield) as a solid.

To a solution of 3-(4-(cyclopent-1-en-1-yl)-6-fluoro-1-oxoisoindolin-2-yl)-3-ethylpiperidine-2,6-dione (208 mg, 0.58 mmol) in THF (10 mL) was added Pd/C (10% content, 200 mg). The mixture was purged with H$_2$ then stirred under H$_2$ for 12 h. The mixture was filtered through a pad of CELITE® and the filtrate was concentrated. The residue was purified using silica gel eluting with DCM/MeOH from 100:1 to 50:1 to give Compound 18 (86.2 mg, 42% yield) as a solid. MS (ESI) m/z 359.1 [M+H]$^+$. $^1$HNMR (DMSO-d$_6$, 400 MHz) δ 10.88 (s, 1H), 7.39-7.35 (m, 1H), 7.23-7.20 (m, 1H), 4.60 (q, J=18.0 Hz, 2H), 3.16-3.08 (m, 1H), 2.58-2.53 (m, 3H), 2.16-2.04 (m, 5H), 1.82-1.78 (m, 2H), 1.68-1.59 (m, 4H), 0.96 (t, J=7.2 Hz, 3H).

Example 19. Compound 19: 3-(4-Cyclopentyl-6-fluoro-1-oxoisoindolin-2-yl)pyrrolidine-2,5-dione

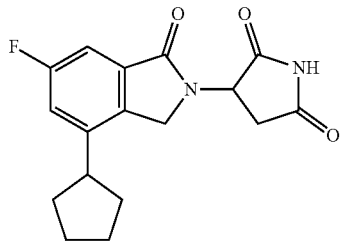 [SMILES: O=C1CC(N2Cc3c(cc(F)cc3C3CCCC3)C2=O)C(=O)N1]

To a solution of methyl 3-bromo-2-(bromomethyl)-5-fluorobenzoate (440 mg, 1.35 mmol) in DMF (5 mL) was added methyl 2,4-diamino-4-oxobutanoate (237 mg, 1.63 mmol) and TEA (411 mg, 4.07 mmol). The mixture was heated at 50° C. for 3 h then concentrated. The residue was purified using silica gel eluting with EA in PE from 0% to 70% to give methyl 4-amino-2-(4-bromo-6-fluoro-1-oxoisoindolin-2-yl)-4-oxobutanoate (336 mg, 69% yield) as a solid.

To a solution of methyl 4-amino-2-(4-bromo-6-fluoro-1-oxoisoindolin-2-yl)-4-oxobutanoate (116 mg, 0.323 mmol) in 1,4-dioxane/H$_2$O (4 mL/0.4 mL) was added 2-(cyclopent-1-en-1-yl)-4,4,5,5-tetramethyl-1,3,2-dioxaborolane (75.2 mg, 0.387 mmol) and K$_2$CO$_3$ (89.2 mg, 0.646 mmol). The mixture was purged with N$_2$ and Pd(dppf)Cl$_2$ (47.3 mg, 0.065 mmol) was added. The mixture was heated at 83° C. overnight then cooled to RT and filtered. The filtrate was concentrated and the residue was purified using silica gel eluting with EA in petroleum from 10% to 80% to give 4-amino-2-(4-(cyclopent-1-en-1-yl)-6-fluoro-1-oxoisoindolin-2-yl)-4-oxobutanoic acid (91 mg, 85% yield) as a solid.

To a solution of 4-amino-2-(4-(cyclopent-1-en-1-yl)-6-fluoro-1-oxoisoindolin-2-yl)-4-oxobutanoic acid (91 mg, 0.27 mmol) in DMF (4 mL) was added CDI (133 mg, 0.822 mmol). The mixture was heated at 83° C. overnight then concentrated, and the residue purified using silica gel eluting with EA in petroleum from 0% to 50% to give 3-(4-(cyclopent-1-en-1-yl)-6-fluoro-1-oxoisoindolin-2-yl)pyrrolidine-2,5-dione (25 mg, 25% yield) as a solid.

To a solution of 3-(4-(cyclopent-1-en-1-yl)-6-fluoro-1-oxoisoindolin-2-yl)pyrrolidine-2,5-dione (44 mg, 0.14 mmol) in MeOH (1 mL) and DCM (2 mL) was added Pd/C (40 mg). The mixture was purged with H$_2$ then stirred under H$_2$ for 12 h. The mixture was filtered and concentrated. The residue was purified by prep-TLC eluting with EA to afford Compound 19 (19.1 mg, 43% yield) as a solid. MS (ESI) m/z 317.0 [M+H]$^+$. $^1$H NMR (400 MHz, DMSO-d$_6$) δ 11.46 (s, 1H), 7.40-7.30 (m, 2H), 5.27 (t, J=8.0 Hz, 1H), 4.69-4.32 (m, 2H), 3.09-3.07 (m, 1H), 2.97-2.94 (m, 2H), 2.04-2.01 (m, 2H), 1.80-1.79 (m, 2H), 1.63-1.60 (m, 4H).

Example 20. Compound 20: 3-(4-Cyclobutyl-6-fluoro-2-isoindolinoyl)-2,6-piperidinedione

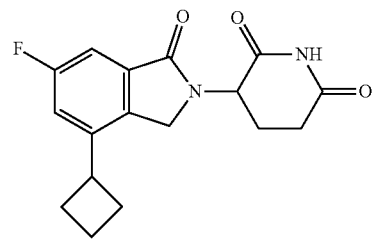 [SMILES: O=C1CCC(N2Cc3c(cc(F)cc3C3CCC3)C2=O)C(=O)N1]

Compound 20 was prepared analogously to Compound 1 but using cyclobutylboronic acid pinacol ester instead of 2-(cyclopent-1-en-1-yl)-4,4,5,5-tetramethyl-1,3,2-dioxaborolane. MS (ESI) m/z 317.0 [M+H]$^+$. $^1$H NMR (400 MHz, DMSO-d$_6$) δ 10.98 (s, 1H), 7.40-7.37 (m, 1H), 7.34-7.32 (m, 1H), 5.11 (dd, J=5.2, 13.2 Hz, 1H), 4.40-4.21 (m, 2H), 3.68-3.60 (m, 1H), 2.95-2.88 (m, 1H), 2.63-2.57 (m, 1H), 2.45-2.40 (m, 1H), 2.33-2.29 (m, 2H), 2.21-2.14 (m, 2H), 2.03-1.96 (m, 2H), 1.86-1.81 (m, 1H).

Example 21. Compound 21: 3-(4-Cyclopentyl-6-fluoro-5-methyl-1-oxoisoindolin-2-yl) piperidine-2,6-dione

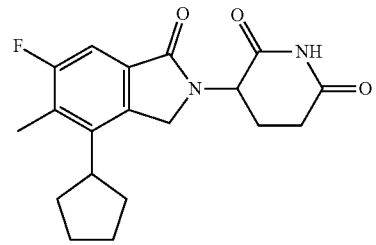 [SMILES: Cc1c(F)cc2c(c1C1CCCC1)CN(C1CCC(=O)NC1=O)C2=O]

To a solution of methyl 2,4-dimethyl-5-fluorobenzoate (0.512 g, 2.81 mmol) in H$_2$O/MeOH (2:2 mL) was added LiOH (0.202 g, 8.43 mmol). After 2 h, the mixture was concentrated and 1N HCl was added until the solution became acidic and a solid precipitated. Filtration gave 2,4-dimethyl-5-fluorobenzoic acid. (0.472 g, quantitative yield) as a solid.

To a solution of 2,4-dimethyl-5-fluorobenzoic acid (0.472 g, 2.81 mmol) in H$_2$SO$_4$ (4 mL) at 0° C. was added NBS (0.505 g, 2.83 mmol). The mixture was stirred overnight at RT then poured into ice and extracted with EA. The organic phase was washed with brine, dried over Na$_2$SO$_4$, and concentrated to give 3-bromo-2,4-dimethyl-5-fluorobenzoic acid (0.513 g, 75% yield) as a solid.

To a solution of 3-bromo-2,4-dimethyl-5-fluorobenzoic acid (0.513 g, 2.08 mmol) in MeOH (12 mL) was added H$_2$SO$_4$ (2 mL) dropwise. The mixture was heated at 60° C. for 16 h. The mixture was concentrated and extracted with EA. The organic phase was washed with water and brine then concentrated. The residue was purified using silica gel eluting with 0% to 10% EA in hexanes to afford methyl 3-bromo-2,4-dimethyl-5-fluorobenzoate (0.400 g, 74% yield) as a solid.

To a solution of methyl 3-bromo-2,4-dimethyl-5-fluorobenzoate (0.400 g, 1.54 mmol) in carbon tetrachloride (10 mL) was added NBS (0.301 g, 1.69 mmol) and benzoyl peroxide (0.074 g, 0.307 mmol). The mixture was heated at 80° C. for 4 h. The mixture was filtered to remove unreactive solids and concentrated to give methyl 3-bromo-2-(bromomethyl)-5-fluoro-4-methylbenzoate.

To a solution of methyl 3-bromo-2-(bromomethyl)-5-fluoro-4-methylbenzoate (0.520 g, 1.54 mmol) in ACN (12 mL) was added tert-butyl 4,5-diamino-5-oxopentanoate (0.366 g, 1.54 mmol) and K$_2$CO$_3$ (0.532 g, 3.85 mmol). The mixture was heated at 60° C. for 6 h. The mixture was concentrated then extracted with EA. The organic phase was washed with water and brine then concentrated. The product was precipitated with diethyl ether to afford tert-butyl 5-amino-4-(4-bromo-6-fluoro-5-methyl-1-oxoisoindolin-2-yl)-5-oxopentanoate (0.359 g, 54% yield) as a solid.

To a solution of tert-butyl 5-amino-4-(4-bromo-6-fluoro-5-methyl-1-oxoisoindolin-2-yl)-5-oxopentanoate (0.209 g, 0.488 mmol) in toluene/water (4 mL/0.4 mL) was added cyclopentene-1-boronic acid, pinacol ester (0.195 g, 0.976 mmol), K$_2$CO$_3$ (0.202 g, 1.465 mmol), and Pd(dppf)Cl$_2$ (0.793 g, 0.976 mmol). The mixture was heated at 90° C. for 16 h then concentrated. The residue was purified using silica gel eluting with EA to afford tert-butyl 5-amino-4-(4-(cyclopent-1-en-1-yl)-6-fluoro-5-methyl-1-oxoisoindolin-2-yl)-5-oxopentanoate. (0.200 g, 98% yield).

To a solution of tert-butyl 5-amino-4-(4-(cyclopent-1-en-1-yl)-6-fluoro-5-methyl-1-oxoisoindolin-2-yl)-5-oxopentanoate (0.203 g, 0.488 mmol) in MeOH (18 mL) was added palladium hydroxide and Pd/C at approximately 0.200 g each. The mixture was purged with H$_2$ and stirred under H$_2$ overnight. The mixture was filtered and concentrated to give tert-butyl 5-amino-4-(4-cyclopentyl-6-fluoro-5-methyl-1-oxoisoindolin-2-yl)-5-oxopentanoate (0.145 g, 71% yield).

To a solution of tert-butyl 5-amino-4-(4-cyclopentyl-6-fluoro-5-methyl-1-oxoisoindolin-2-yl)-5-oxopentanoate (0.145 g, 0.346 mmol) in DCM (2 mL) was added TFA (2 mL). After 1 h, the solution was concentrated to give 5-amino-4-(4-cyclopentyl-6-fluoro-5-methyl-1-oxoisoindolin-2-yl)-5-oxopentanoic acid (0.125 g, 99% yield).

To a solution of 5-amino-4-(4-cyclopentyl-6-fluoro-5-methyl-1-oxoisoindolin-2-yl)-5-oxopentanoic acid (0.125 g, 0.346 mmol) in ACN (5 mL) was added CDI (0.281 g, 1.73 mmol), and TEA (241 μm, 1.73 mmol). After 16 h, the mixture was concentrated and extracted with EA. The organic phase was washed with brine, dried over Na$_2$SO$_4$, filtered, concentrated, and triturated with ether to afford Compound 21 (0.08 g, 8% yield). MS (ESI) m/z 344.4 [M+H]$^+$. $^1$H NMR (400 MHz, DMSO-d$_6$) δ 10.975 (s, 1H), 7.31 (d, 1H), 5.11-5.08 (dd, 1H), 4.51-4.84 (d, 1H), 4.38-4.34 (d, 1H), 2.93-2.86 (t, 1H), 2.60-2.49 (d, 2H), 2.44-2.41 (d, 1H), 2.31 (s, 3H), 2.025-1.99 (m, 3H), 1.83 (m, 2H), 1.68-1.66 (m, 5H), 1.50-1.46 (m, 1H).

Example 22. Compound 22: 3-{4-[(S)-2,2,2-Trifluoro-1-methylethyl]-6-fluoro-2-isoindolinoyl}-2,6-piperidinedione

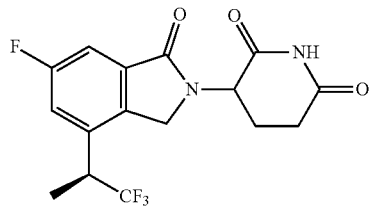 [SMILES: C[C@@H](c1cc(F)cc2c1CN(C1CCC(=O)NC1=O)C2=O)C(F)(F)F]

Compound 22 was prepared under analogous reaction conditions used for compounds described herein but using 3-fluoro-5-methoxycarbonylphenylboronic acid pinacol ester and 2-bromo-3,3,3-trifluoropropene under palladium coupling conditions followed by: reduction using H$_2$ and Pd/C; bromination using NBS and AIBN; and addition of 3-aminopiperidine-2,6-dione using TEA. Chiral separation of the crude final product afforded Compound 22. MS (ESI) m/z 359.0 [M+H]$^+$.

Example 23. Compound 23: 3-{4-[(R)-2,2,2-Trifluoro-1-methylethyl]-6-fluoro-2-isoindolinoyl}-2,6-piperidinedione

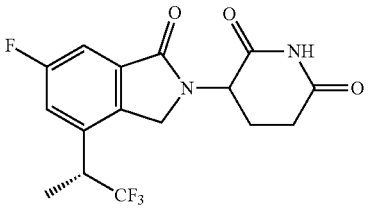 [SMILES: C[C@H](c1cc(F)cc2c1CN(C1CCC(=O)NC1=O)C2=O)C(F)(F)F]

Compound 23 was prepared under analogous reaction conditions used for compounds described herein but using 3-fluoro-5-methoxycarbonylphenylboronic acid pinacol ester and 2-bromo-3,3,3-trifluoropropene under palladium coupling conditions followed by: reduction using H$_2$ and Pd/C; bromination using NBS and AIBN; and addition of 3-aminopiperidine-2,6-dione using TEA. Chiral separation of the crude final product afforded Compound 23. MS (ESI) m/z 359.0 [M+H]$^+$.

Example 24. Compound 24: 3-(4-Cyclopentyl-5-fluoro-2-isoindolinoyl)-2,6-piperidinedione

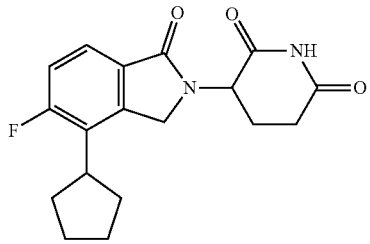 [SMILES: O=C1CCC(N2Cc3c(ccc(F)c3C3CCCC3)C2=O)C(=O)N1]

Compound 24 was prepared analogously to Compound 1 but using tert-butyl 5-amino-4-(4-bromo-5-fluoro-1-oxoisoindolin-2-yl)-5-oxopentanoate instead of tert-butyl 5-amino-4-(4-bromo-6-fluoro-1-oxoisoindolin-2-yl)-5-oxopentanoate. MS (ESI) m/z 331.1 [M+H]$^+$. $^1$H NMR (400 MHz, DMSO-d$_6$) δ 11.00 (s, 1H), 7.62-7.59 (m, 1H), 7.33-7.28 (m, 1H), 5.11 (dd, J=4.8, 12.8 Hz, 1H), 4.54 (d, J=17.2 Hz, 1H), 4.37 (d, J=17.2 Hz, 1H), 3.15-3.08 (m, 1H), 2.96-2.87 (m, 1H), 2.62-2.58 (m, 1H), 2.44-2.41 (m, 1H), 2.01-1.99 (m, 3H), 1.82-1.74 (m, 4H), 1.69-1.65 (m, 2H).

Example 25. Compound 25: 3-[6-Fluoro-4-(2-norbornanyl)-2-isoindolinoyl]-2,6-piperidinedione

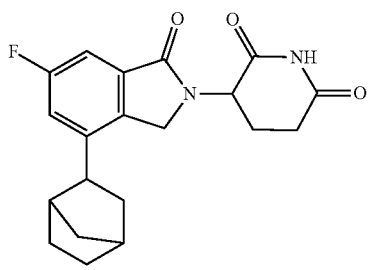 [SMILES: O=C1CCC(N2Cc3c(cc(F)cc3C3CC4CCC3C4)C2=O)C(=O)N1]

Compound 25 was prepared analogously to Compound 1 but using 2-(bicyclo[2.2.1]heptan-2-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 356.4 [M+H]$^+$. $^1$H NMR (400 MHz, DMSO-d$_6$) δ 11.024 (s, 1H), 7.35 (s, 2H), 5.125 (d, 1H), 4.49 (d, 1H), 4.3 (d, 1H), 2.94-2.876 (t, 1H), 2.61-2.58 (d, 1H), 2.49-2.37 (m, 2H), 2.32 (s, 1H), 2.01-1.99 (m, 1H), 1.92-1.86 (m, 1H), 1.56-1.51 (m, 3H), 1.44-1.40 (m, 2H), 1.29-1.24 (m, 1H), 1.11-1.07 (m, 1H).

Example 26. Compound 26: 3-[4-(2,2-Dimethylcyclopentyl)-6-fluoro-2-isoindolinoyl]-2,6-piperidinedione

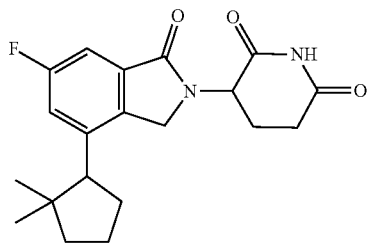 [SMILES: CC1(C)CCCC1c1cc(F)cc2c1CN(C1CCC(=O)NC1=O)C2=O]

Compound 26 was prepared analogously to Compound 1 but using 2-(5,5-dimethylcyclopent-1-enyl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 358.4 [M+H]$^+$. $^1$H NMR (400 MHz, DMSO-d$_6$) δ 11.024 (s, 1H), 7.381 (s, 2H), 5.14-5.12 (d, 1H), 4.504 (d, 1H), 4.276 (d, 1H), 2.94-2.821 (m, 2H), 2.63-2.57 (d, 1H), 2.49-2.43 (m, 1H), 2.063-2.017 (m, 3H), 1.82 (m, 1H), 1.70 (m, 1H), 1.63 (m, 2H), 0.960-0.94 (d, 3H), 0.745 (s, 3H).

Example 27. Compound 27: 3-(4-Cyclopentyl-7-fluoro-2-isoindolinoyl)-2,6-piperidinedione

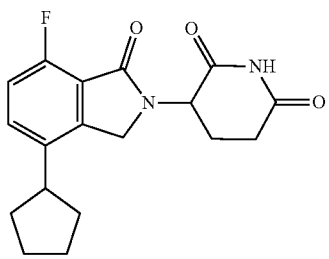 [SMILES: O=C1CCC(N2Cc3c(C4CCCC4)ccc(F)c3C2=O)C(=O)N1]

Compound 27 was prepared analogously to Compound 1 but using 5-amino-4-(4-bromo-7-fluoro-1-oxoisoindolin-2-yl)-5-oxopentanoate instead of 5-amino-4-(4-bromo-6-fluoro-1-oxoisoindolin-2-yl)-5-oxopentanoate. MS (ESI) m/z 330.3 [M+H]$^+$. $^1$H NMR (400 MHz, DMSO-d$_6$) δ 11.01 (s, 1H), 7.53-7.56 (d, 1H), 7.21-7.25 (t, 1H), 5.07-5.11 (m, 1H), 4.49-4.53 (d, 1H), 4.33-4.37 (d, 1H), 3.00-3.07 (m, 1H), 2.91-2.96 (m, 1H), 2.56-2.61 (m, 1H), 2.44-2.49 (m, 1H), 1.98-2.05 (m, 3H), 1.78-1.82 (m, 2H), 1.56-1.79 (m, 4H).

Example 28. Compound 28: 3-(6-Chloro-4-cyclopentyl-2-isoindolinoyl)-2,6-piperidinedione

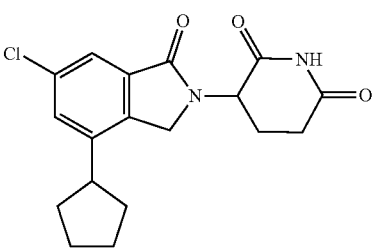 [SMILES: O=C1CCC(N2Cc3c(cc(Cl)cc3C3CCCC3)C2=O)C(=O)N1]

Compound 28 was prepared analogously to Compound 1 but using 5-amino-4-(4-bromo-6-chloro-1-oxoisoindolin-2-yl)-5-oxopentanoate instead of 5-amino-4-(4-bromo-6-fluoro-1-oxoisoindolin-2-yl)-5-oxopentanoate. MS (ESI) m/z 347.1[M+H]+. 1H NMR (400 MHz, DMSO-d6) δ 11.00 (s, 1H), 7.56 (s, 2H), 5.12 (dd, J=4.8, 13.2 Hz, 1H), 4.53-4.32 (m, 2H), 3.08-3.04 (m, 1H), 2.97-2.90 (m, 1H), 2.88-2.87 (m, 1H), 2.44-2.40 (m, 1H), 2.05-2.00 (m, 3H), 1.82-1.80 (m, 2H), 1.63-1.58 (m, 4H).

Example 29. Compound 29: 3-[4-Cyclopentyl-6-(trifluoromethyl)-2-isoindolinoyl]-2,6-piperidinedione

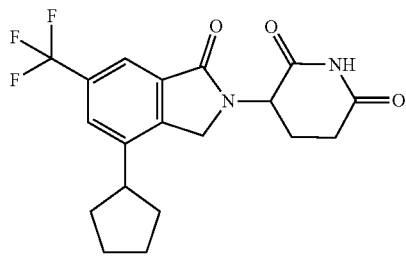 [SMILES: O=C1CCC(N2Cc3c(cc(C(F)(F)F)cc3C3CCCC3)C2=O)C(=O)N1]

Compound 29 was prepared analogously to Compound 1 but using 5-amino-4-(4-bromo-6-trifluoromethyl-1-oxoisoindolin-2-yl)-5-oxopentanoate instead of 5-amino-4-(4-bromo-6-fluoro-1-oxoisoindolin-2-yl)-5-oxopentanoate. MS (ESI) m/z 381 [M+H]+. 1H NMR (400 MHz, DMSO-d6) δ 11.02 (s, 1H), 7.83 (m, 2H), 5.16 (dd, J=5.2, 13.2 Hz, 1H), 4.65-4.44 (m, 2H), 3.18-3.13 (m, 1H), 2.96-2.88 (m, 1H), 2.67-2.59 (m, 1H), 2.49-2.42 (m, 1H), 2.05-2.02 (m, 4H), 1.89-1.82 (m, 1H), 1.69-1.61 (m, 4H).

Example 30. Compound 30: 3-{4-[(S)-2,2,2-Trifluoro-1-methylethyl]-2-isoindolinoyl}-2,6-piperidinedione

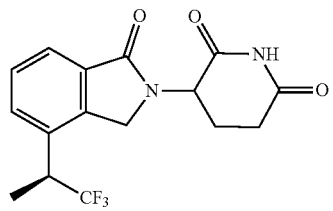 [SMILES: C[C@@H](c1cccc2c1CN(C1CCC(=O)NC1=O)C2=O)C(F)(F)F]

Compound 30 was prepared under analogous reaction conditions used for compounds described herein but using methyl 2-methyl-3-(4,4,5,5-tetramethyl-1,3,2-dioxaborolan-2-yl)benzoate and 2-bromo-3,3,3-trifluoropropene under palladium coupling conditions followed by: reduction using H2 and Pd/C; bromination using NBS and AIBN; and addition of 3-aminopiperidine-2,6-dione using TEA. Chiral separation of the crude final product afforded Compound 30. MS (ESI) m/z 341.1 [M+H]+.

Example 31. Compound 31: 3-{4-[(R)-2,2,2-Trifluoro-1-methylethyl]-2-isoindolinoyl}-2,6-piperidinedione

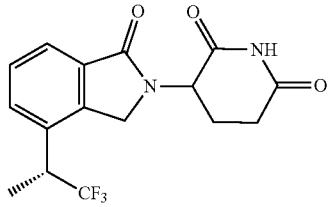 [SMILES: C[C@H](c1cccc2c1CN(C1CCC(=O)NC1=O)C2=O)C(F)(F)F]

Compound 31 was prepared under analogous reaction conditions used for compounds described herein but using methyl 2-methyl-3-(4,4,5,5-tetramethyl-1,3,2-dioxaborolan-2-yl)benzoate and 2-bromo-3,3,3-trifluoropropene under palladium coupling conditions followed by: reduction using H2 and Pd/C; bromination using NBS and AIBN; and addition of 3-aminopiperidine-2,6-dione using TEA. Chiral separation of the crude final product afforded Compound 31. MS (ESI) m/z 341.1 [M+H]+.

Example 32. Compound 32: 3-[6-Fluoro-4-(tetrahydro-2H-pyran-4-yl)-2-isoindolinoyl]-2,6-piperidinedione

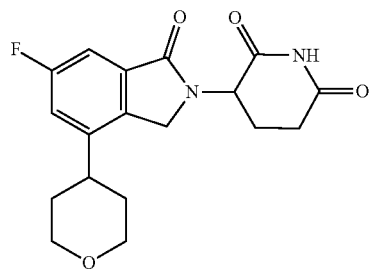 [SMILES: O=C1CCC(N2Cc3c(cc(F)cc3C3CCOCC3)C2=O)C(=O)N1]

Compound 32 was prepared analogously to Compound 1, but using 2-(3,6-dihydro-2H-pyran-4-yl)-4,4,5,5-tetramethyl-1,3,2-dioxaborolane instead of 2-(cyclopent-1-en-1-yl)-4,4,5,5-tetramethyl-1,3,2-dioxaborolane. MS (ESI) m/z 347.1 [M+H]+.

Example 33. Compound 33: 3-(4-(sec-butyl)-6-fluoro-1-oxoisoindolin-2-yl)piperidine-2,6-dione

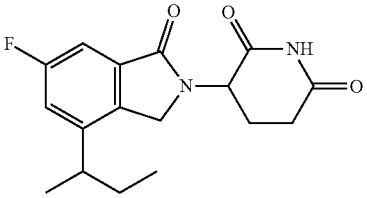 [SMILES: CCC(C)c1cc(F)cc2c1CN(C1CCC(=O)NC1=O)C2=O]

Compound 33 was prepared analogously to Compound 1 but using 4,4,5,5-tetramethyl-2-(1-methylethenyl)-1,3,2-dioxaborolane instead of 2-(cyclopent-1-en-1-yl)-4,4,5,5-tetramethyl-1,3,2-dioxaborolane. MS (ESI) m/z 319.1 [M+H]+.

Example 34. Compound 34: 3-(6-fluoro-4-isopropyl-1-oxoisoindolin-2-yl)piperidine-2,6-dione

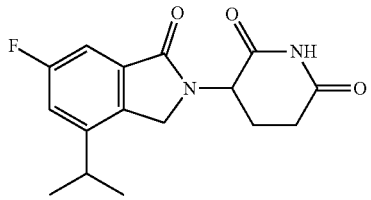 [SMILES: CC(C)c1cc(F)cc2c1CN(C1CCC(=O)NC1=O)C2=O]

Compound 34 was prepared analogously to Compound 1 but using 2-buten-2-ylboronic acid pinacol ester instead of 2-(cyclopent-1-en-1-yl)-4,4,5,5-tetramethyl-1,3,2-dioxaborolane. MS (ESI) m/z 305.1 [M+H]$^+$.

Example 35. Biological Assays

Western Blot Analysis

MV-4-11 cells were grown in RPMI 1640 media supplemented with 10% fetal bovine serum, streptomycin and penicillin.

Cells were cultured at approximately 10$^6$ cells per mL and incubated in DMSO or the indicated compounds for 6-8 hours. Whole cell extracts were prepared using RIPA lysis buffer according to manufacturer's protocol (Pierce). Briefly, 4×10$^6$ cells were washed once in PBS, the cell pellets were resuspended in RIPA lysis buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies: Anti-PDE6D antibody: Santa Cruz Biotechnology, sc-166854 (Dallas, Tex.); Anti-Ikaros: Abcam, ab191394 (Cambridge, Mass.); anti-CK1α antibody: Abcam, ab108296 (Cambridge, Mass.); β-Actin (8H10D10) mouse monoclonal antibody: Cell Signaling Technology, #3700 (Danvers, Mass.); IRDye 680RD Goat anti-rabbit antibody: LI-COR, 926-68071 (Lincoln, Nebr.); and IRDye 800CW Goat anti-mouse antibody: LI-COR, 926-32210 (Lincoln, Nebr.).

The data for degradation of cellular CK1α, PDE6D and Ikaros are shown below in Table 1. The % degradation values are reported as "A", "B", "C", or "D." "A" represents a % degradation value of less than 25% (value<25%); "B" represents a % degradation value of equal to or more than 25% and less than 50% (25%≤value<50%); "C" represents a % degradation value of equal to or more than 50% and less than 75% (50%≤value<75%); and "D" represents a % degradation value of equal to or more than 75% (value≥75%). DM50 was used as control.

TABLE 1

Activities of Compounds in Various Degradation Assays tested at 1 μM

| Compound No. | % Degradation compared to DMSO | | |
|---|---|---|---|
| | PDE6D | CK1α | Ikaros |
| 1 | D | D | C |
| 2 | D | B | A |
| 3 | D | C | B |
| 4 | A | A | A |
| 5 | D | D | B |
| 6 | D | B | A |
| 7 | D | A | A |
| 8 | A | A | A |
| 9 | D | A | A |
| 10 | C | A | B |
| 11 | D | B | D |
| 12 | D | A | A |
| 13 | C | C | C |
| 14 | B | B | C |
| 15 | D | C | B |
| 16 | D | C | A |
| 17 | C | n.a. | D |
| 18 | B | A | A |
| 19 | D | A | A |
| 20 | D | C | B |
| 21 | D | B | B |
| 22 | D | D | A |
| 23 | B | C | A |
| 24 | B | A | A |
| 25 | C | B | B |
| 26 | C | A | B |
| 27 | A | A | A |
| 28 | A | A | A |
| 29 | A | A | B |
| 30 | A | A | B |
| 31 | A | B | C |
| 32 | D | B | A |
| 33 | D | D | A |
| 34 | D | C | A |

Furthermore, Compounds 1 and 22 were tested against a comparative compound A in the PDE6D degradation assay at 1 μM. Compound A did not demonstrate any measurable PDE6D degradation activity and the results are summarized in the table below. "A" represents a % degradation value of less than 25% (value<25%) and "D" represents a % degradation value of equal to or more than 75% (value≥75%).

| Compound | % Degradation of PDE6D |
|---|---|
| A | A |
| 1 | D |
| 22 | D |

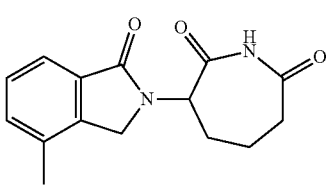

Compound A

Cell-Based Assay

Either frozen primary blood mononuclear cells (PBMCs) or frozen CD14+ mobilized peripheral blood monocytes were purchased from AllCells (PB003F, Normal Peripheral Blood MNC (Alameda, Calif.)). Cells were quick thawed, washed 1-time with RPMI-1640 (10% FBS/1% Pen-Strep)

and plated in 96 well plates at 200,000 cells per well. Cells were pretreated with DMSO only or with the indicated compound for 1 h and then induced with 100 ng/mL lipopolysaccharide (LPS) for 18-24 h. The supernatant was analyzed for IL-1β, IL-6, and TNFα, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc., San Diego, Calif.). After washing with PBS, the indicated compound was added (50 μL/well) followed by PBMCs diluted at 3-4 million cells/mL (150 μL/well). Plates were incubated for 24 h and the supernatants collected for Mesoscale IL-2 analysis. IL-2 activity is measured as fold difference from the DMSO control.

IL-1β, IL-6 and TNFα activities were tested at two different concentrations (1 μM and 10 μM) and the results are shown in Tables 2 and 3 respectively. IL-2 activity was also tested at two different concentrations (1 μM and 10 μM) and the results are shown in Table 4.

In Tables 2 and 3, the % inhibition values are reported as "A", "B", "C", or "D." "A" represents a % inhibition value of less than 10% (value<10%); "B" represents a % inhibition value of equal to or more than 10% and less than 25% (10%≤value≤25%); "C" represents a % inhibition value of equal to or more than 25% and less than 50% (25%≤value≤50%); and "D" represents a % inhibition value of equal or more than 50% (value≥50%).

In Table 4, the fold-change values are reported as "A", "B", "C", or "D". "A" represents a fold-change value of equal to or less than 0.5 (value≤0.5); "B" represents a fold-change value of more than 0.5 and equal to or less than 1 (0.5<value≤1); "C" represents a fold-change value of more than 1 and less than 1.5 (1<value<1.5); and "D" represents a fold-change value of equal to or more than 1.5 (value≥1.5).

TABLE 2

Activities of compounds in IL-1β, IL-6 and TNFα inhibition assays (Compounds tested at 1 μM).

| Compound No. | IL-1β | IL-6 | TNFα |
|---|---|---|---|
| 1 | B | A | C |
| 2 | A | B | A |
| 3 | A | A | A |
| 4 | A | A | C |
| 5 | C | A | C |
| 6 | A | A | B |
| 7 | A | B | A |
| 8 | A | B | B |
| 9 | A | B | A |
| 10 | A | A | B |
| 11 | A | A | A |
| 12 | A | A | B |
| 13 | C | A | D |
| 14 | A | A | B |
| 15 | A | A | A |
| 16 | A | A | A |
| 17 | A | A | C |
| 18 | A | A | A |
| 19 | A | A | A |
| 20 | A | A | B |
| 21 | A | A | A |
| 22 | A | A | A |
| 23 | A | A | A |
| 24 | A | A | B |
| 25 | A | A | B |
| 26 | A | A | A |
| 27 | A | B | B |
| 28 | A | A | B |
| 29 | A | B | A |
| 30 | A | A | A |
| 31 | A | A | A |
| 32 | A | A | A |
| 33 | A | A | C |
| 34 | A | A | C |

TABLE 3

Activities of compounds in IL-1β, IL-6 and TNFα inhibition assays (Compounds tested at 10 μM).

| Compound No. | IL-1β | IL-6 | TNFα |
|---|---|---|---|
| 1 | C | A | C |
| 2 | B | B | B |
| 3 | A | A | A |
| 4 | B | A | D |
| 5 | D | A | D |
| 6 | B | A | D |
| 7 | A | A | B |
| 8 | A | B | C |
| 9 | A | B | C |
| 10 | B | B | D |
| 11 | A | A | A |
| 12 | A | A | C |
| 13 | C | A | D |
| 14 | B | A | C |
| 15 | A | A | A |
| 16 | A | A | B |
| 17 | B | A | C |
| 18 | B | A | C |
| 19 | A | A | A |
| 20 | A | A | C |
| 21 | A | A | C |
| 22 | B | B | C |
| 23 | A | A | C |
| 24 | A | A | A |
| 25 | C | A | B |
| 26 | A | A | B |
| 27 | A | A | C |
| 28 | A | B | B |
| 29 | A | A | B |
| 30 | A | A | B |
| 31 | A | A | B |

TABLE 4

Activities of compounds in IL-2 inhibition assay (Compounds tested at 1 and 10 μM).

| Compound No. | 1 μM | 10 μM |
|---|---|---|
| 1 | A | A |
| 2 | B | B |
| 3 | A | A |
| 4 | B | B |
| 5 | A | A |
| 6 | B | A |
| 7 | C | B |
| 8 | B | B |
| 9 | B | B |
| 10 | C | B |
| 11 | B | B |

TABLE 4-continued

Activities of compounds in IL-2 inhibition assay (Compounds tested at 1 and 10 μM).

| Compound No. | % Induction compared to DMSO | |
| --- | --- | --- |
| | 1 μM | 10 μM |
| 12 | B | B |
| 13 | D | D |
| 14 | B | B |
| 15 | B | A |
| 16 | B | B |
| 17 | B | B |
| 18 | C | B |
| 19 | B | B |
| 20 | A | A |
| 21 | A | A |
| 22 | A | A |
| 23 | B | B |
| 24 | C | C |
| 25 | C | B |
| 26 | B | B |
| 27 | B | B |
| 28 | C | B |
| 29 | B | B |
| 30 | C | B |
| 31 | B | B |
| 33 | A | n.a. |
| 34 | A | n.a. |

Furthermore, Compounds 1 and 22 were tested against a comparative compound B in the IL-2 inhibition assay at 10 μM. Compound B induced IL-2 (upregulation) and both Compounds 1 and 22 demonstrated strong inhibition of IL-2 (downregulation). The results are summarized in the table below. "A" represents a fold-change value of equal to or less than 0.5 (value≤0.5) and "D" represents a fold-change value of equal to or more than 1.5 (value≥1.5).

| Compound | % Induction compared to DMSO |
| --- | --- |
| B | D |
| 1 | A |
| 22 | A |

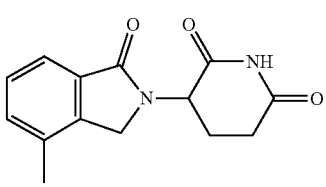

Compound B

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (Ia):

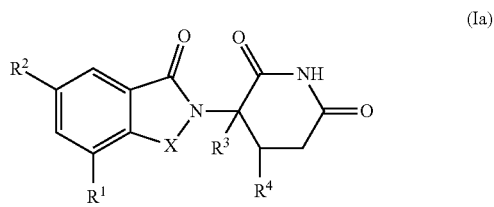

or a pharmaceutically acceptable salt thereof, wherein:
X is $CH_2$ or C=O;
$R^1$ is unsubstituted $C_3$-$C_8$ cycloalkyl or unsubstituted $C_4$-$C_8$ cycloalkenyl;
$R^2$ is halogen;
$R^3$ is hydrogen, deuterium, fluoro, or methyl; and
$R^4$ is hydrogen or methyl.

2. The compound of claim 1, wherein $R^1$ is unsubstituted $C_3$-$C_8$ cycloalkyl.

3. The compound of claim 1, wherein $R^1$ is cyclopropyl, cyclobutyl, cyclopentyl, cyclohexyl, or cycloheptyl.

4. The compound of claim 1, wherein $R^1$ is cyclopentenyl or cyclohexenyl.

5. The compound of claim 1, wherein $R^3$ is hydrogen, deuterium, fluoro, or methyl.

6. The compound of claim 5, wherein $R^3$ is hydrogen or methyl.

7. The compound of claim 1, wherein $R^4$ is hydrogen or methyl.

8. A compound selected from:

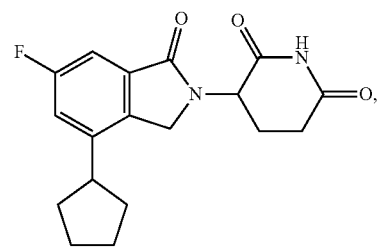

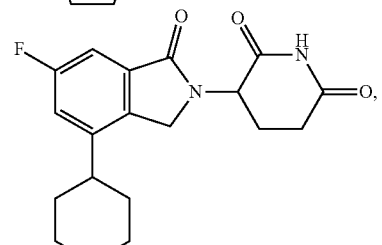

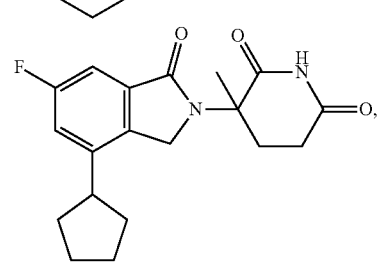

-continued and pharmaceutically acceptable salts thereof.

9. A pharmaceutical composition comprising a compound of claim 1, or a pharmaceutically acceptable salt thereof, and at least one pharmaceutically acceptable excipient or carrier.

10. A method of inhibiting the activity of a protein in one or more cells of a biological sample, comprising contacting a compound of claim 1, or a pharmaceutically acceptable salt thereof with the cells in the biological sample, wherein the protein is PDE6, CK1α, or ikaros.

11. A method of modulating the activity of a cytokine in one or more cells of a biological sample, comprising contacting a compound of claim 1, or a pharmaceutically acceptable salt thereof with the cells in the biological sample.

12. The compound of claim 1, wherein X is $CH_2$.

13. The compound of claim 1, wherein X is C=O.

14. The compound of claim 1, wherein $R^1$ is cyclopropyl.

15. The compound of claim 1, wherein $R^1$ is cyclobutyl.

16. The compound of claim 1, wherein $R^1$ is cyclopentyl.

17. The compound of claim 1, wherein $R^1$ is cyclohexyl.

18. The compound of claim 1, wherein $R^2$ is fluoro or chloro.

19. The compound of claim 1, wherein $R^2$ is fluoro.

20. The compound of claim 1, wherein $R^2$ is chloro.

21. The compound of claim 1, wherein $R^3$ is hydrogen.

22. The compound of claim 1, wherein $R^4$ is hydrogen.

* * * * *